US007005271B1

(12) United States Patent
Freyssinet et al.

(10) Patent No.: US 7,005,271 B1
(45) Date of Patent: Feb. 28, 2006

(54) METHOD FOR THE DETERMINATION OF THE PRETHROMBOTIC STATE

(75) Inventors: Jean-Marie Freyssinet, 18, rue Himmerich, F-67000 Strasbourg (FR); Benedicte Antoni, Strasbourg (FR); Frederic Donie, Penzberg (DE); Helmut Lill, Wielenbach (DE)

(73) Assignees: Jean-Marie Freyssinet, Strasbourge (FR); Bénédict Hugel, Oberhaslach (FR)

( * ) Notice: Subject to any disclaimer, the term of this patent is extended or adjusted under 35 U.S.C. 154(b) by 852 days.

(21) Appl. No.: 09/588,553

(22) Filed: Jun. 7, 2000

Related U.S. Application Data

(63) Continuation of application No. 08/750,776, filed as application No. PCT/EP95/02846 on Jul. 19, 1995, now abandoned.

(30) Foreign Application Priority Data

Jul. 23, 1994 (EP) .................................. 94111514

(51) Int. Cl.
*C07K 14/745* (2006.01)
*C12N 9/74* (2006.01)
*C12Q 1/37* (2006.01)
*G01N 33/543* (2006.01)
*G01N 33/554* (2006.01)

(52) U.S. Cl. ..................... 435/7.92; 435/7.2; 435/7.21; 435/7.24; 435/7.5; 435/7.72; 435/7.8; 435/7.91; 435/7.94; 435/13; 435/23; 435/24; 435/174; 435/176; 435/177; 435/212; 435/214; 436/506; 436/518; 436/519; 436/528; 436/531; 436/534; 436/538; 436/69; 436/71; 530/381; 530/384; 530/388.7; 530/389.6

(58) Field of Classification Search ................. 435/7.2, 435/7.21, 7.24, 7.5, 7.71, 7.72, 7.8, 7.92, 435/7.94, 13, 23–26, 174, 176, 177, 212, 435/214; 436/506, 518, 519, 528, 531, 534, 436/538, 69, 71; 530/380, 381, 384, 388.7, 530/389.6
See application file for complete search history.

(56) References Cited

U.S. PATENT DOCUMENTS

| 4,668,638 | A | 5/1987 | Janoff et al. ................. 436/506 |
| 5,266,462 | A | 11/1993 | Hemker et al. ............... 436/69 |
| 5,340,719 | A | 8/1994 | Hajek et al. ................. 435/7.21 |
| 5,561,070 | A | 10/1996 | Stewart et al. .............. 436/518 |

FOREIGN PATENT DOCUMENTS

| AU | 22948/88 | 4/1989 |
| DE | 42 29 933 | 3/1994 |
| WO | 95 08121 | 3/1995 |

OTHER PUBLICATIONS

Connor et al., May 1989, Differentiation-dependent expression of phosphatidylserine in mammalian plasma membranes: quantitative assessment of outer-leaflet lipid by prothrombinase complex formation. Proc. Natl. Acad. Sci. 86: 3184-3188.*
Thiagarajan et al., Dec. 1991. Collagen-induced exposure of anionic phospholipid in platelets and platelet-derived microparticles. J. Biol. Chem. 266: 24302-24307.*
Rote et al., Mar. 1993. Immunologic detection of phosphatidylserine externalization during thrombin-induced platelet activation. Clin. Immunol. Immunopathol. 66: 193-200.*
Koopman et al. Sep. 1994. Annexin V for flow cytometric detection of phosphatidylserine expression on B cells undergoing apoptosis. Blood 84: 1415-1420.*
Abrams et al, 1991, Immunological detection of activated plateles in clinical disorders. Thromb. Haemostasis 65: 467-473.
Dachary-Prigent et al, May 15, 1993. Annexin V as a probe of aminophospholipid exposure . . . Blood 81: 2554-2565.
Wharram et al 1991, Tissue factor expression in endothelial cell/monocyte cocultures . . . J. Immunol. 146: 1437-1445.
Margel et al, 1982. Polyacrolein microspheres as a new tool in cell biology. Cell Sci. 56: 157-175.
Isenberg et al, 1986, Topographic distribution of a granule membrane protein (GMP-140) . . . Blood Cells 12: 191-204.
Harlow et al., 1988. *Antibodies, A Laboratory Manual*, Cold Spring Harbor Laboratory, pp. 605, 608, 612.
Allen et al, 1992. The circulating phagocyte reflects the in vivo state of immune defense. Current Opinion in Infectious Diseases, 5: 389-398.
King, 1984. Simultaneous detection of two cell surface antiges . . . J. Immunological Meth. 72: 481-88.
Rinder et al., 1991. Progressive platelet activation with storage . . . Transfusion 31: 409-414.
Goding, . . , 1983. *Monoclonal Antibodies: Principles and Practice*, Academic Press, London, pp. 75-79.

* cited by examiner

*Primary Examiner*—Long V. Le
*Assistant Examiner*—James L. Grun
(74) *Attorney, Agent, or Firm*—Rothwell, Figg, Ernst & Manbeck, P.C.

(57) ABSTRACT

The present invention relates to determining the prethrombotic state, in particular determining an amount or presence of circulating microparticles and/or stimulated procoagulant cells.

10 Claims, 11 Drawing Sheets

METHOD FOR THE DETERMINATION OF THE PRETHROMBOTIC STATE

CROSS REFERENCE TO RELATED APPLICATION

This application is a continuation application of U.S. application Ser. No. 08/750,776, filed Dec. 19, 1996, now abandoned, the disclosure of which is hereby incorporated by reference, which is a 35 U.S.C. 371 filing of PCT/EP95/02846 filed Jul. 19, 1995.

The present invention relates to a method for determining the prethrombotic state of an individual. More specifically the present invention relates to a method for the determination of the circulating microparticles and/or stimulated procoagulant cells, to a method for the determination of a special category of circulating microparticles and/or stimulated procoagulant cells as well as to a method for the determination of phospholipid-binding antibodies which are related to diseases which are related to an increased thrombotic risk.

Thrombosis occurs as an acute event which cannot be easily and rapidly predicted. Various permissive conditions for the development of thrombotic complications have been described, inflammation being the most common. Alterations of blood and/or vascular cell functions are probably at the origin of prethrombotic states and could therefore be indicative of the associated thrombotic risk provided they could be unambiguously assessed.

Anionic phospholipids, chiefly phosphatidyl serine, are essential for normal hemostasis, but they are almost entirely sequestered in the inner leaflet of the plasma membrane of resting blood and vascular cells (Devaux P. F., Static and dynamic lipid asymmetry in cell membranes. Biochemistry 30 (1991), 1163–1173; Zwaal R. F. A et al., Mechanism and function of changes in membrane-phospholipid asymmetry in platelets and erythrocytes. Biochem. Soc. Trans. 21 (1993), 248–253). Their catalytic potential is due to ability to assemble the characteristic enzyme complexes of the blood coagulation cascade (FIG. 1) at the site of a wound. As yet almost all of available kinetic data of coagulation reactions have been gained at saturating phospholipid concentrations (Mann K. G. et al., Surface-dependent hemostasis. Semin. Hematol. 29 (1992), 213–226). This does probably not reflect physiological conditions and it is reasonable to expect that the degree of exposure of anionic phospholipids should be a rate-limiting factor. Asymmetric distribution of the different phospholipid species within the plasma membrane could involve an ATP-dependent aminophospholipid transporter termed "inward" aminophospholipid translocase (Devaux P. F., Static and dynamic lipid asymmetry in cell membranes. Biochemistry, 30 (1991), 1163–1173). Following appropriate stimulation, exposure of anionic phospholipids towards the external leaflet of the membrane can take place. Thrombin, collagen and, above all the thrombin+collagen combination are the major physiological agonists of anionic phospholipid exposure in platelets. It occurs as a scrambling process responsible for membrane remodelling and microparticle shedding (Zwaal R. F. A et al., Mechanism and function of changes in membrane-phospholipid asymmetry in platelets and erythrocytes. Biochem. Soc. Trans. 21 (1993), 248–253). Phospholipid scrambling and vesiculation could be the consequence of transient elevation of intracellular calcium. Moreover, the recently described thrombin receptor of platelets, also present in endothelial cells, stimulates calcium influx (Coughlin S. R. et al., Characterization of a functional thrombin receptor. J. Clin. Invest. 89 (1992), 351–355) and could then be involved in such processes. Under pathological circumstances, the terminal membrane-attack complement complex C5b-9 could also provoke the shedding of microparticles bearing a proportion of anionic phospholipids from platelets and endothelium (Zwaal R. F. A et al., Mechanism and function of changes in membrane-phospholipid asymmetry in platelets and erythrocytes. Biochem. Soc. Trans. 21 (1993), 248–253; Hamilton K. et al., Complement proteins C5b-9 induce vesiculation of the endothelial plasma membrane and expose catalytic surface for assembly of the prothrombinase complex. J. Biol. Chem. 265 (1990), 3809–3814). Furthermore endotoxin could induce a similar behaviour of monocytes Robinson R. A. et al., Endotoxin enhances the expression of monocyte prothrombinase activity. Blood, 79 (1992) 406–416; Satta N. et al., Monocyte vesiculation, J. Immunol. 153 (1994), 3245–3255: A mechanism for dissemination of membrane-associated procoagulant activities following stimulation by lipopolysaccaride (1994). More drastic conditions such as apoptosis and/or cell lysis result in membrane fragmentation responsible for circulating particles having phospholipid-dependent procoagulant activity.

Phosphatidylserine is thought to be a determinant of reticuloendothelial recognition leading to elimination of circulating membrane debris (Allen T. et al., phosphatidylserine as a determinant of reticuloendothelial recognition of liposome models of the erythrocyte surface. Proc. Natl. Acad. Sci USA 85 (1988), 8067–8071). However, it is conceivable that in case of continuous cell membrane damage the reticuloendothelial system could be overwhelmed and that excess of anionic phospholipid could progressively trigger coagulation reactions. Under such circumstances the release of sequestered phospholipids could be at the origin of the anti-phospholipid syndrome associated with thrombosis (McNeil et al., Immunology and clinical importance of antiphospholipid antibodies. Adv. Immunol. 49 (1991), 193–280). In addition, some tumorigenic cells express higher amount of phosphatidyl serine in their outer membrane leaflet than their differentiated non-tumorigenic counterpart (Connor J. et al., Differentiation-dependent expression of phosphadityl serine in mammal plasma membranes: Quantitative assessment of outer leaflet lipid by prothrombinase complex formation. Proc. Natl. Acad. Sci. USA 86 (1989), 3184–3188). Several studies on (circulating) microparticles or procoagulant cells have already been published (Abrams C. & Shattil S. J, Immunological detection of activated platelets in clinical disorders. Thromb. Haemostats. 65 (1991), 67–473; Nomura S. et al., Antiplatelet autoantibody-related microparticles in patients with idiopathic (autoimmune) thrombocytopenic purpura. Ann. Hematol, 62 (1991), 103–107; Nomura S. et al., Microparticle generation during in vitro platelet activation by anti-CD9 murine monoclonal antibodies. Thrombos. Res. 62 (1991), 429–439; Tans G. et al., Comparison of anticoagulant and procoagulant activities of stimulated platelets and platelet-derived microparticles. Blood 77 (1991), 2641–2648; Gilbert G. E. et al., Platelet-derived microparticles express high affinity receptors for factor VIII. J. Biol. Chem. 266 (1991), 17261–17268; Bode A. P. et al. Vesiculation of platelets during in vitro aging. Blood 77, (1991), 887–895; Owens M. R. et al., Platelet microvesicles adhere to subendothelium and promote adhesion of platelets. Thrombos. Res. 66 (1992), 247–258; Hoffmann M. et al., Coagulation factor IXa binding to activated platelets and platelet-derived microparticles: a flow cytometric study. Thromb. Haemostas. 68 (1992), 74–78; Jy W. et al., Clinical significance of platelet microparticles in autoimmune thrombocytopenias. J. Lab. Clin. Med. 119 (1992) 334–345; Borenstain-Ben Yashar V. et al., Phosphatidyl serine in the outer leaflet of red blood cells from β-thalassemia patients may explain the chronic hypercoagulable state and thrombotic episodes. Am. J. Hematol. 44 (1993), 63–65; Wiedmer T. et al., Complement-induced vesiculation and exposure of membrane prothrombinase sites in platelets of paroxysmal nocturnal hemoglobinuria, Blood 82 (1993) 1192–1196; Lee Y. et al., Elevated microparticles in transient ischemic attacks, lacunar infarcts, and multiinfarct dementias. Thrombosis Res. 72 (1993) 295–304; Galli M. et al., Effect of antiphospholipid antibodies on procoagulant activity of activated platelets and platelet-derived microparticles. Br. J. Haemotol. 83 (1993), 466–472; Rajesekhar D. et al., Procoagulant activity of platelet-derived microparticles in whole blood: Differences between adults and neonates. Blood 82 (1983), 163a; Jy W. et al., Platelet microparticles adhere to polymorphonuclear leukocytes: Possible mode of clearance. Blood 82 (1993), 281a; Jy W. et al., Procoagulant activity of platelet microparticles (PAPM) correlates with thrombotic risks. Blood 82 (1993), 281a) and their clinical significance has been discussed (Zucker-Franklin D., Clinical significance of platelet microparticles. J. Lab. Clin. Med. 119 (1992), 321–322). In one of the above studies (Lee Y. et al., Elevated microparticles in transient ischemic attacks, lacunar infarcts, and multi-infarct dementias. Thrombosis Res. 72 (1993) 295–304), the pharmacological control of the extent of platelet vesiculation appeared feasible. At the opposite of membrane vesiculation and phosphatidyl serine exposure tendencies, Scott syndrome, a rare bleeding disorder, is characterized by a reduced ability of platelets, erythrocytes and lymphocytes to expose an appropriate membrane-associated procoagulant activity (Bevers E. M. et al., Defective $Ca^{2+}$-induced microvesiculation and deficient expression of procoagulant acitivty in erythrocytes from a patient with a bleeding disorder: A study of the red blood cells of Scott syndrome. Blood 79 (1992), 380–388).

The generation of thrombin is the culminating event of the coagulation cascade, mainly due to a high potential of auto-amplification expressed in several feedback loops (Mann K. G., Krishnaswamy S. & Lawson J. H. Surface-dependent hemostasis. Semin. Hematol., 29 (1992), 213–226), one of them resulting in the exposure of procoagulant phospholipids by and from platelets (Zwaal R. F. A, Comfurius P. & Bevers E. M. Mechanism and function of changes in membrane-phospholipid asymmetry in platelets and erythrocytes. Biochem. Soc. Trans. 21 (1993), 248–253). Excessive thrombin generation can be controlled by two different mechanisms, either by direct neutralization by anti-thrombins or by anticoagulant protein C which acquires the capacity of degrade procoagulant cofactors VIIIa & Va after activation by thrombin itself (FIG. 1) (Mann K. G., Krishnaswamy S. & Lawson J. H. Surface-dependent hemostasis. Semin. Hematol, 29 (1992), 213–226; Esmon C. T., The roles of protein C and thrombomodulin in the regulation of blood coagulation. J. Biol. Chem. 264 (1989), 4743–4746). An increase of activated/stimulated cells and circulating procoagulant cell fragments could result in excessive thrombin generation in the early stage following cell damage or activation. Supplementary exposure of procoagulant phospholipids could then become a consequence of the amplification of thrombin production. This should help to explain how sequestered phospholipids can acquire antigenic potential following exposure, especially when it is pointed out that the resulting phospholipid-binding antibodies are associated with thrombosis (McNeil et al., Immunology and clinical importance of antiphospholipid antibodies. Adv. Immunol. 49 (1991), 193–280). One possible explanation could be the interference of anti-phospholipid antibodies in the anticoagulant protein C pathway (Freyssinet J.-M. et al., An IgM lupus anticoagulant that neutralizes the enhancing effice of phospholipids on purified endothelial thrombomodulin. A mechanism for thrombosis. Thromb. Haemostats. 55 (1986), 309–313) as confirmed by several groups of investigators but other mechanisms should not be ruled out (McNeil et al., Immunology and clinical importance of antiphospholipid antibodies. Adv. Immunol. 49 (1991), 193–280). Once exposed, phosphatidyl serine could bind certain plasma proteins thus forming complex antigens. The diversity of such possible complexes could explain the diversity of associated clinical manifestations with the presence of resulting antibodies (Freyssinet J.-M. et al., Phospholipid-binding antibodies and thrombosis. Blood Coagulat. Fibrinol., 4 (1993), 645–648).

Previous methods for assaying coagulation reactions are in the great majority of cases an estimation of clotting time such as the prothrombin time. These determinations give no information on the procoagulant activity or prethrombotic state of an individual because as indicated above the data have been gained at saturating phospholipid concentrations.

WO 93/24840 describes a method for determining the procoagulant activity of resting platelets based on the availability of negatively charged phospholipids in the outer membrane of platelets. The amount of procoagulant phospholipids in whole blood is low, because resting platelets have a mechanism to transport phosphatidyl serine from the outer to the inner leaflet of the membrane. A minor amount of the phosphatidyl serine is probably still present in the outer leaflet causing a residual procoagulant activity of the platelets. This residual or resting activity establishes a threshold at above which activated clotting factors may result in thrombosis. Thus, the susceptibility of an individual to experience thrombosis may be correlated with the level of procoagulant activity of his platelets.

However, there is no absolute proof that this method by determining the activity of resting platelets is directly related to the prethrombotic state of an individual. Therefore, there is still a need for a simple and more direct method for the determination of the prethrombotic state of an individual. Since not only platelets are activated in the coagulation reaction and are releasing microparticles or fragments rich in phospholipids there is also still a need for a method for determining the origin of microparticles and stimulated procoagulant cells or fragments thereof in the blood of an individual.

The object of the present invention was to find a simple and rapid method for the determination of the prethrombotic state of an individual and for the diagnosis of various vascular diseases such as peripheral arterial occlusion, arterosclerosis, diabetic angiopathy, vasculitis, pre-eclampsia, lupus erythematosus or angina pectoris and for the diagnosis and monitoring the state of an individual after PTCA (percutaneous transluminal coronaroangioplasty).

Some auto-immune disorders and other diseases, for example infection, inflammation, neoplasia myocardialinfaction strokes or transient ischaemic attacks, venous thrombosis, arterial thrombosis, pregnancy screening, connective tissue disease, thrombocytopenia, oral contraceptive therapy, migraine/headaches or pulmonary hypertension, are correlated with the occurrence of phospholipid-binding antibodies. Phospholipid-binding antibodies are heterogeneous immunoglobulins of the G, M or A class. Some of these auto-antibodies recognize phospholipids (anionic or/and hexagonal phase) in connection with other proteins which could be exposed on the outer surface of microparticles and/or procoagulant cells. Examples for such proteins are β2-GP-I (β2-glycoprotein-I), prothrombin, protein C and protein S (Triplett, D. A. Antiphospholipid antibodies and thrombosis. A consequence, coincidence, or cause ? Arch. Pathol. Lab. Med., 1993, 117 78–88; Oosting et al., Antiphospholipid antibodies directed against a combination of phospholipids with prothrombin, protein C, protein S: An explanation for their pathogenic mechanisms Blood, 1993, 81, 2618–2625). There is a need for a simple method for the detection of these phospholipid-binding antibodies.

Apoptosis, or programmed cell death, could result in increased circulating cell fragments containing phosphatidyl-serin (so called apoptotic bodies). The detection of circulating apoptotic bodies bearing exposed phosphatidylserine could be helpful for the diagnosis of high levels of in vivo apoptosis associated with major diseases such as AIDS, cancer, autoimmune disorders or artherosclerosis. The level of circulating apoptotic bodies could be indicative of the development or evolution of the disease especially, if the cellular origin of the microparticles can be determined.

In accordance with the present invention there is provided a simple and rapid method for determining the Prethrombotic state of an individual and for the diagnosis of various vascular diseases such as peripheral arterial occlusion, artheriosclerosis, diabetic angiopathy, vasculitis, pre-eclampsia, lupus erythematosus or angina pectoris and for the diagnosis and monitoring the state of an individual after PTCA (percutaneous transluminal coronaroangioplasty) by determining the circulating microparticles and/or stimulated procoagulant cells. It was found that the amount of circulating microparticles and/or stimulated procoagulant cells in the blood of an individual correlates with the prethrombotic sate of this individual as well as with the above mentioned vascular diseases. These analyses could also be used for the diagnosis of risk factors and for the monitoring the state of an individual after PTCA With this method it is also possible to determine circulating apoptotic bodies of various origin which are associated with diseases leading to cell damage for example AIDS, cancer, autoimmune disorders or artherosclerosis. Furtheron, by the term microparticles it is understood to include these apoptotic bodies of various origin.

Especially there is provided by the present invention a method for determining the circulating microparticles and/or stimulated procoagulant cells by mixing a sample containing said circulating microparticles and/or stimulated procoagulant cells with a specific receptor for a compound exposed on said microparticles and procoagulant cells which receptor is bound directly or indirectly to a solid phase under conditions to form a complex of the solid phase bound receptor and the microparticle or procoagulant cell, separating the solid phase from the liquid phase and determining the amount of microparticles and/or procoagulant cells on the solid phase or after separation of the solid phase by appropriate methods (FIG. 2).

Besides this heterogeneous method for the determination it is also possible to use homogeneous methods, i.e. methods wherein no separation of the solid phase from a liquid phase is necessary. Therefore by the present invention there is also provided a method for determining the circulating microparticles and/or stimulated procoagulant cells by mixing a sample containing said circulating microparticles and/or stimulated procoagulant cells with a specific receptor for a compound exposed on said circulating microparticles and/or stimulated procoagulant cells under conditions to form a complex of the circulating microparticles and/or stimulated procoagulant cells and the receptor and determining the amount of microparticles and/or stimulated procoagulant cells by appropriate methods. If a precipitation or agglutination should find place, the receptor must be at least bivalent. In this case, the amount of microparticles and/or stimulated procoagulant cells could be determined by nephelometric or turbidimetric measurement.

In another embodiment a variation of the above assay can be used for determining a special category of circulating microparticles and/or stimulated procoagulant cells by mixing a sample containing said circulating microparticles and/or stimulated procoagulant cells with a specific receptor 1 for a compound exposed on said microparticles and stimulated procoagulant cells which receptor is bound directly or indirectly to a solid phase under conditions to form a complex of the solid phase bound receptor 1 and the microparticle or procoagulant cell, optionally separating the solid phase from the liquid phase, binding of a receptor 2 to the microparticles and/or the procoagulant cells which receptor 2 is specific for a marker of the special category of microparticles and stimulated procoagulant cells and determining the complex of receptor 1, microparticles or stimulated procoagulant cell and receptor 2 by appropriate methods (FIG. 2).

In another variation of the assay for the determination of the special subgroup or category of the circulating microparticles and/or stimulated procoagulant cells the sample is mixed with a receptor for a subgroup-specific compound exposed on said microparticles and/or stimulated procoagulant cells and determining the binding of circulating microparticles or stimulated procoagulant cells to said receptor by appropriate methods. The subgroup-specific receptor must be directed to a compound which is exposed only on circulated microparticles and/or stimulated procoagulant cells and not on resting cells. Examples for these receptors are annexin-V for exposed procoagulant phospholipid patch, specific antibodies to the active/functional conformation of the platelet membrane glycoprotein complex GPIIb/IIIa, or the monocyte or lymphocyte adhesive receptor LFA-1, or endothelial thrombomodulin.

Annexin-V and procoagulant phospholipid patch:
Dachary-Prigent J. et al., Annexin-V as a probe of aminophospholipid exposure and platelet membrane vesiculation: A flow cytometry study showing a role for free sulfhydryl groups. Blood 81, 2554–2565

GPIIb/IIIa:
Abrams C. & Shattil S. J., Immunological detection of activated platelets in clinical disorders. Thromb. Haemostats. 65 (1991), 67–473

LFA-I:
Sattan N. et al., Monocyte vericulation, J. Immunol. 153 (1994), 3245–3255: A mechanism for dissemination of membrane-associated procoagulant activities following stimulation by lipopolysaccaride (1994), submitted;
Hedman H. and Lundgren E. Regulation of LFA-I activity in human B cells. J. Immunol. 149 (1992), 2295–2299

Thrombomodulin:
Hamilton K. et al., Complement proteins C5b-9 induce vesiculation of the endothelial plasma membrane and expose catalytic surface for assembly of the prothrombinase complex. J. Biol. Chem. 265 (1990), 3809–3814

In another embodiment a variation of the above assay can be used for the detection of phospholipid-binding antibodies in a blood sample mixing the blood sample with microparticles and/or stimulated procoagulant cells or synthetic phospholipid-containing liposomes under conditions to allow the binding of phospholipid-binding antibodies present in said blood sample to said microparticles, stimulated procoagulant cells or synthetic phospholipid-containing liposomes determining the phospholipid-binding antibodies by appropriate methods (FIG. 3).

DETAILED DESCRIPTION OF THE INVENTION

The detection and characterization of stimulated or activated blood and/or vascular cells and shed procoagulant microparticles can be considered as a key step in the understanding of the pathogenesis of thrombosis. Circulating stimulated or activated (the two terms could be used for the same expression) procoagulant cells or fragments and microparticles derived therefrom appear as markers of prethrombotic states and also disseminate coagulation reactions. Such a dual behaviour requires assessment on quantitative and qualitative basis. The detection procedure has to be fast to allow appropriate prevention of the development of thrombosis.

The invention provides a method for determining the prethrombotic state of an individual and for the diagnosis of various vascular diseases and risk factors and for monitoring the state of an individual after PTCA by determining the circulating microparticles and/or stimulated procoagulant cells. The term microparticles means small particles which are derived from stimulated procoagulant cells mainly platelets by microparticle shedding (Zwaal R. F. A. et. al., Mechanism and function of changes in membrane-phospholipid asymmetry in platelets and erythrocytes. Biochem. Soc. Trans. 21 (1993), 248–253). The term procoagulant cells means whole stimulated procoagulant cells as well as fragments thereof which expose anionic phospholipids on their outer surface. The term microparticles within this definition includes also apoptotic bodies of various origin as described above.

For the determination of these microparticles and/or stimulated procoagulant cells any appropriate method such as homogeneous or heterogeneous immunoassays or functional assays could be used.

Since the concentration of these circulating microparticles and stimulated procoagulant cells in the blood is rather low it is preferred that the first step of the present method is a binding of these microparticles or cells to a solid phase via binding to a specific receptor. Thereby a concentration and separation of these microparticles and cells from other blood cells and other blood or vascular compounds is possible.

Nevertheless, it is also possible to determine the microparticles and/or stimulated procoagulant cells by a homogeneous method without an intermediate separation step. For example the microparticles and/or stimulated procoagulant cells could be precipitated or agglutinated by a receptor which is at least bivalent. The precipitation or agglutination could be measured directly for example by nephelometric or turbidimetric measurement. It is also possible to measure the concentration by other homogeneous methods such as an (electro)chemiluminescent method (EP-A-0 580 979, WO 87/06706). In this case the receptor can also be monovalent.

As specific receptor any receptor which binds to a naturally occurring molecule on the surface of the microparticles and stimulated procoagulant cells could be used. Such a molecule must be specific for the microparticles and stimulated procoagulant cells. Specific means that this molecule or marker must be exposed only on these microparticles or cells and not on resting cells e.g. resting platelets or that this molecule or marker is exposed in a larger amount on the surface of the microparticles or stimulated cells compared to the precursor cells. Preferably the receptor is directed to the phospholipids on the surface of the microparticles and stimulated procoagulant cells. Annexin, especially Annexin-V, a phospholipid- and calcium-binding protein also referred to as placental anticoagulant protein-I or vascular anticoagulant-α (Barton G. J. et al., Amino acid sequence analysis of the annexin super-gene family of proteins. Eur. J. Biochem. 198 (1991), 749–760), has been characterized as a structural and functional probe (Mosser G. et al., Subdomain structure of lipid-bound annexin-V resolved by electron image analysis. J. Mol. biol. 217 (1991), 241–245; Ravanat C. et al., Use of annexin-V and its binding to lipid vesicles. J. Mol. Biol. 226 (1992), 1271–1278; Ravanat C. et al., A neutron solution scattering study of the structure of annexin-V to demonstrate the role of phosphatidylserine exposure in the maintenance of haemostatic balance by endothelial cells. Biochem J. 282 (1992), 7–13; Freyssinet J.-M. et al., The catalytic role of anionic phospholipids in the activation of protein C by factor Xa and expression of its anticoagulant function in human plasma Blood Coagulat. Fibrinol. 2 (1991), 691–698) of catalytic phospholipids in coagulation reactions. In the presence of calcium, annexin-V behaves as a strong antagonist of phospholipid-dependent coagulation reactions due to its potent ability to compete with vitamin K-dependent proteins for binding to anionic phospholipid surfaces (Ravanat C. et al., A neutron solution scattering study of the structure of annexin-V to demonstrate the role of phosphatidylserine exposure in the maintenance of haemostatic balance by endothelial cells. Biochem J. 282 (1992), 7–13). It was therefore surprising that annexin-V could be used in a diagnostic method for the determination of microparticles and/or stimulated procoagulant cells without negatively altering the phospholipid-dependent coagulation reaction. Other specific receptors are for example phospholipid-binding antibodies or antibodies directed to proteins embedded in the phospholipids of the microparticles.

The specific receptors such as annexin, especially annexin-V or specific antibodies to compounds exposed on the surface of microparticles and stimulated procoagulant cells could be coated directly to the surface of a solid phase by methods known in the art such as adsorption or covalent coupling via bifunctional agents. The indirect binding of the specific receptors to the solid phase is preferred because thereby it is possible to use universally coated solid phases such as streptavidin-coated solid phases and because a preincubation of the specific receptor with the sample in liquid phase is possible. In some cases thereby the binding of the receptor to the microparticles and/or stimulated procoagulant cells could be enhanced. The specific receptor is bound in this case to the solid phase via a specific binding pair comprising of a first and a second binding pair member (bpm). The first bpm is attached to the solid phase and the second bpm is coupled to the specific receptor. Examples of specific binding pairs are known in the art for example hapten/antibody, enzyme/substrate, enzyme/inhibitor, antigen/antibody, avidin or streptavidin/biotin and sugar/lectin. The use of avidin or streptavidin/biotin as the specific binding pair is preferred (FIG. 2). The procedure of attachment of avidin or streptavidin and the coupling of biotin to proteins and other molecules is well known in the art for example Bayer and Wilchek, Methods of Biochemical Analysis (1980) 26, 1–45. Streptavidin-coated tubes or microtiter plates are available commercially.

As solid phase there could be used for example tubes, beads, microtiterplates or microcarriers made of plastics for example polystyrol, polyvinyl, polypropylene, polycarbonate, polysaccharide, silicone or glass (E. T. Maggio, Enzyme Immunoassays, CAP. Press, Florida (1980), 175–180, EP-A-0 063064, Bioengineering 16 (1974), 997–1003 and Sonderson and Wilson, Immunology 20 (1971), 1061–1065). The microcarriers could be used as small columns.

As sample it is possible to use whole blood or plasma. It is especially preferred to use platelet poor plasma. Preferably the sample is supplemented with an anticoagulant solution containing for example thrombin and factor Xa inhibitors. The composition of the anticoagulant solution for collection of blood samples should keep platelet activation at a level as low as possible.

The microparticles and/or stimulated procoagulant cells are captured by incubating the sample with the specific receptor attached to the solid phase or by incubating the sample with a soluble specific receptor and thereafter attaching the receptor to the solid phase. The incubation period depends on the specific receptor i.e. its affinity, and the shape of the solid phase. When using biotinylated annexin-V attached to a streptavidin-coated microtiterplate an incubation period of about 30 minutes at room temperature is appropriate. For the optimal binding of annexin-V to aminophospholipids free calcium ions should be present during the incubation in an amount of at least 1 mM but not exceeding 10 mM.

After this incubation period the solid phase should be washed to remove unbound sample compounds. A buffer solution with physiological salt concentrations and calcium ions for example 50 mM Tris buffer, pH 7,5 containing 0,1 M NaCl and 1 mM $CaCl_2$ could be used.

After capturing of the microparticles and/or stimulated procoagulant cells the amount of these compounds could be determined directly on the solid phase or after the separation of the compounds from the solid phase. When using tubes or microtiterplates as solid phase it is preferred to determine the amount directly on this solid phase. When using a short column filled with microcarriers as solid phase it is preferred to eluate the microparticles and/or activated cells from the column and thereafter determine the amount in the eluant. Because the measurement directly on the solid phase is more rapid this method is more convenient and preferred.

For the determination of the amount of microparticles and/or stimulated procoagulant cells on the solid phase or after the separation of the solid phase any appropriate method is convenient. Preferably the microparticles and/or stimulated procoagulant cells are determined via their procoagulant activity which is based on the availability of anionic phospholipids in the outer membrane of the microparticles and/or stimulated procoagulant cells (FIG. 2). The microparticles and/or stimulated procoagulant cells are incubated with a substrate which can be activated by an enzyme or enzyme complex which is procoagulant phospholipid-dependent, such as prothrombin (factor II). Further enzymes, coenzymes and cations such as factor V, factor Xa and calcium-ions, which are required for the activation reaction are added. The prothrombin activation is linearly dependent on the amount of procoagulant anionic phospholipids in the sample. It is preferred to incubate the microparticles and/or stimulated cells in a first step with a mixture of the necessary enzymes, coenzymes and cations for example prothrombin (factor II), factor V, factor Xa and calcium ions. After a predetermined incubation period the activation of prothrombin (factor II) to thrombin (factor IIa) is stopped for example by the complexation of calcium-ions. EDTA is a preferred complexation agent. Thereafter a chromogenic substrate that could be hydrolysed by thrombin is added and the liberation of the chromophore is measured by recording the absorbance change. Chromogenic substrates for thrombin are well known in the art for example Chromozym® TH (Tos-Gly-Pro-Arg-p-nitroanilide-dehydrochlorid) or D-Phe-pipecolyl-Arg-p-nitroanilidedihydrochlorid. The phospholipid-dependent prothrombin-converting activity assay was adapted from Connor J. et al., Differentiation-dependent expression of phosphaditylserine in mammalian plasma membranes: Quantitative assessment of outer leaflet lipid by prothrombinase complex formation. Proc. Natl. Acad. Sci. USA 86 (1989), 3184–3188. Concentration of the various reagents is such that linearity is preserved over a wide concentration range of exposed procoagulant phospholipids. The preferred final concentration of each compound is 2.5 $\mu$M for factor II 33 pM for factor V, 11 pM for factor Xa, 1.3 mM for $CaCl_2$, 5 mM for EDTA, and 70 $\mu$M for Chromozym® TH (Connor J. et al., Differentiation-dependent expression of phosphaditylserine in mammalian plasma membranes: Quantitative assessment of outer leaflet lipid by prothrombinase complex formation. Proc. Natl. Acad. Sci. USA 86 (1989), 3184–3188).

The determination of the microparticles and/or stimulated cells via their procoagulant activity could be used generally e.g. microparticles and/or cells bound to solid phase or liberated of from solid phase.

For the determination of the microparticles and/or stimulated procoagulant cells bound to the solid phase it is also preferred to use a second receptor which is specific for a molecule on the surface of the microparticles and/or stimulated procoagulant cells. The detection is carried out by a sandwich-assay which is well known in the art. The second receptor could be the same as the first receptor or it could be directed against a different molecule or epitope exposed on the surface of the microparticles and/or stimulated procoagulant cells. This molecule exposed on the surface of the microparticles and/or stimulated procoagulant cells could be a molecule that is specific for these cells i.e. a molecule that is not or much less present on resting cells. This molecule could also be a common molecule exposed on stimulated and resting cells. It is only necessary that one of the two receptors used in the sandwich assay is specific for the microparticles and/or stimulated procoagulant cells. This could be the first or the second receptor.

For the determination of the total amount of microparticles and/or stimulated procoagulant cells it is prefered to use receptors directed to compounds which are common to all microparticles and/or stimulated procoagulant cells. Preferably the second receptor is an antibody or annexin-V. Preferred are antibodies directed to anionic phospholipids (Rote et al., Immunologic detection of phosphadityl serine externalization during thrombin-induced platelet activation, Clin. Immunol. Immunopathol. 66 (1993), 193–200; Nomura et al. Anti-phospholipid antibodies bind to platelet microparticles in idiopathic autoimmune thrombocytopenic purpura. Ann. Hematol. 65 (1992)) or annexin-V (Dachary-Prigent J. et al, Annexin-V as a probe of aminophospholipid exposure and platelet membrane vesiculation: A flow cytometry study showing a role for free sulfhydryl groups. Blood 81 2554–2565).

The binding of the second receptor is detected by appropriate methods. The second receptor could be labelled by an enzyme, (electro)chemiluminescent, fluorescent or any other label. It is also possible to use an indirect label, i.e. a receptor for example an antibody directed against the second receptor which is labelled with the above mentioned labels. This indirect label has the advantage that a "universal label" for example a labeled anti-Fc antibody could be used. Examples and methods for the directly or indirectly labeling of the second receptor are known in the art (Coligan J. E., Kruibeek A. M., Margulies D. H., Shevach E. M., and Strober W. (1992, 1994) Current protocols in Immunology—Wiley Interscience—New York).

In the homogeneous method for the determination of the circulating microparticles and/or stimulated procoagulant cells the sample is incubated with a specific receptor. This receptor must be directed to a molecule which is common to all microparticles and/or stimulated procoagulant cells for example anionic phospholipids.

In the case of an agglutination or precipitation reaction the receptor must be at least bivalent to allow the bridging of at least two microparticles and/or stimulated procoagulant cells which results in a precipitation or agglutination. The receptor is preferably an antibody. It is also possible to use monovalent receptors such as annexin-V or bivalent receptors which are cross-linked or coupled to carriers to produce receptor-complexes which are at least bivalent. Methods for cross-linking of receptors or coupling of receptors to carriers such as bovine serum albumin, dextrans, polysaccharides or latex particles are known in the art.

The precipitation or agglutination of the receptor—microparticles and/or stimulated procoagulant cell-complexes are determined preferably by nephelometric or turbidimetric methods.

In another embodiment of the heterogeneous method as described above the first receptor is directed to a compound common to all microparticles and/or stimulated procoagulant cells and the second receptor is directed to a compound, molecule or marker on the surface of the microparticles and/or stimulated procoagulant cells which is common to a subgroup or category of microparticles and stimulated cells (FIG. 2). Thereby it is possible to determine the special category of the microparticles and/or stimulated procoagulant cells and thereby conclude to the origin of the microparticles and/or stimulated procoagulant cells. The origin could be for example thrombocytes, monocytes or endothelial cells.

A further embodiment of the present invention is therefore a method for the determination of a subgroup or category of circulating microparticles and/or stimulated procoagulant cells by mixing a sample containing said circulating microparticles and/or stimulated procoagulant cells with a specific receptor 1 for a compound exposed on said microparticles and stimulated procoagulant cells which receptor is bound directly or indirectly to a solid phase under conditions to allow the formation of a complex of solid phase bound receptor 1 and microparticle or procoagulant cell optionally separating the solid phase from the liquid phase, binding of a receptor 2 to the microparticles and/or procoagulant cells which receptor 2 is specific for a marker of the category or subgroup of microparticles and procoagulant cells and determining the complex of receptor 1, microparticle or stimulated procoagulant cell or receptor 2 by appropriate methods.

As receptor 2 it is preferred to use an antibody against a subgroup-specific marker, molecule or compound on the surface of the microparticles and stimulated cells. Examples for these markers are for thrombocytes GPIb, GPIX, GPIIb/IIIa, thrombospondin or for endothelial cells, thrombomodulin or for monocytes CD14 or TF (tissue factor which could also be found on micorparticles shed from stimulated endothelium) or GMP 140 (P-selectin) which is found both on activated platelets and endothelial cells or CD4 and DC11a for apoptotic bodies.

A further embodiment of the present invention is a modification of this assay for the determination of the subgroup of circulating microparticles and/or stimulated procoagulant cells. This method for the determination of subgroups of microparticles and/or stimulated procoagulant cells comprises mixing a sample with a receptor for a subgroup-specific compound expose on the microparticles and/or stimulated procoagulant cells and determining the binding of this receptor by appropriate methods. A receptor for a subgroup-specific compound means a receptor that is directed to a compound, molecule or marker which is only present on the subgroup and is not or much less present on other subgroups of microparticles and/or stimulated procoagulant cells and resting cells for example resting platelets, monocytes or endothelial cells. For example some phospholipid-binding antibodies are directed to proteins in connection with phospholipids, i.e. they do not bind much to the protein or the phospholipid alone.

This binding of this subgroup-specific receptor to the microparticles and/or stimulated procoagulant cells could be determined by known methods. The subgroup-specific receptor could be for example bound directly or indirectly to a solid phase as described above. After capturing the microparticles and/or stimulated procoagulant cells of a special subgroup the amount could be determined directly on the solid phase or after their separation from the solid phase as described above for example via their procoagulant activity (prothromin assay) or via a second receptor which is specific for the microparticles and/or stimulated procoagulant cells or a receptor which is specific for a marker on resting cells such as platelets, monocytes or endothelial cells. The binding of the subgroup-specific receptor could also be determined directly via the precipitation or agglutination of the microparticles and/or stimulated procoagulant cells by this receptor which must be in this case at least bivalent as described above. To obtain an agglutination the subgroup-specific receptor is coupled to particles such as latex particles.

With the aid of the above described assays it is not only possible to detect circulating microparticles and/or stimulated procoagulant cells or subgroups thereof. These assays could be slightly modified to determine phospholipid-binding antibodies in a sample. Therefore, there is provided a method for determining phospholipid-binding antibodies in a sample by mixing the sample with microparticles and/or stimulated procoagulant cells or synthetic phopholipid-containing liposomes under conditions to allow the binding of phospholipid-binding antibodies to these microparticles or procoagulant cells or synthetic phospholipid-containing liposomes and determining the binding of the phospholipid-binding antibodies by appropriate methods.

The microparticles and/or stimulated procoagulant cells can be obtained from human blood or plasma especially from human platelet poor plasma. It is also possible to use microparticles and/or stimulated procoagulant cells from blood or plasma of an animal since phospholipids are ubiquitous components. It is preferred to use synthetic liposomes containing phospholipids in their membrane. Methods for the production of liposomes are known in the art for example Freyssinet et al., Biochem. J. (1989), 261, 341–348. A preferred method is to use liposomes made of a mixture of phosphatidyl serine and phosphatidyl choline (1:2) prepared by the dialysis method according to Freyssinet et al. (above).

The microparticles and/or stimulated procoagulant cells or liposomes can be bound to a solid phase preferably by receptors to phospholipids i.e. phospholipid-binding antibodies or annexin-V. The receptors could be bound directly or indirectly to the solid phase as described above (FIG. 3).

In the preferred embodiment the microparticles, stimulated procoagulant cells or liposomes are bound to a solid phase via streptavidin or avidin/biotin. Streptavidin- or avidin-coated solid phases are known in the art. The microparticles or procoagulant cells or liposomes are biotinylated. Biotinylation of these microparticles, cells or liposomes can be done by incorporation of biotinylated phospholipids into the membrane of these particles. This could be done by simply adding to the microparticles, stimulated procoagulant cells or liposomes biotinylated phospholipids for example biotinylated phosphatidyl ethanolamine or phosphatidyl choline. The biotinylated phospholipids are inserted into the membrane of the particles. It is especially preferred to use this method for attaching synthetically produced liposomes to solid phase. The liposomes are produced by adding for example 1% biotinylated phosphatidyl ethanolamine or biotinylated phosphatidyl choline to the other phospholipids.

In another preferred embodiment the circulating microparticles and/or stimulated procoagulant cells or synthetic phospholipid-contining liposomes are bound to a annexin-V-coated solid phase as described above (FIG. 3).

The blood sample under examination is mixed with the microparticles and/or procoagulant cells or liposomes under conditions to allow the binding of phospholipid-binding antibodies in said blood sample to the particles and to allow the binding of the particles to the solid phase in the case of an indirect attachment. The particles could be attached to the solid phase simultaneously, before or after the binding of the antibodies to the particles. After a separation of the solid phase and the liquid phase to remove any unbound compounds and if necessary an additional wash step of the solid phase, the phospholipid-binding antibodies which are bound to the solid phase via the microparticles, stimulated procoagulant cells or liposomes are determined by appropriate methods.

It is preferred to determine the bound phospholipid-binding antibodies by specific labelled receptors to the phospholipid-binding antibodies such as anti-Fc antibodies, anti-human immunglobuline antibodies, anti-human-IgA, G, M-antibodies, anti-light-chain-antibodies, protein A or protein G. The specific receptors for the phospholipid-binding antibodies could be labelled directly or indirectly as described supra.

This method for the determination of phospholipid-binding antibodies can be variated to detect special subgroups of phospholipid-binding antibodies. It is known that some auto-antibodies are specific for a complex of phospholipids and special proteins which are incorporated or bound to the membrane of the microparticles and/or stimulated procoagulant cells. It is thereby possible to assess combinations of phospholipid-containing particles and phospholipid-binding proteins from plasma for example β2-glycoprotein 1, prothrombin, protein S or protein C as possible antigens responsible for the anti-phospho-lipid syndrome characterized by the presence of corresponding reactive antibodies. The first advantage of this system is its versatility with respect of phospholipids of various composition to be assayed in combination with the above mentioned phospholipid-binding proteins. The second is that it allows to assay the possible in vitro anticoagulant potential of some phospholipid-binding antibodies using the same support as that enabling their detection.

By using microparticles and/or stimulated procoagulant cells or synthetic phospholipid-containing liposomes which further comprise these mentioned proteins it is possible to determine subgroup-specific phospholipid-binding antibodies (FIG. 3). The proteins can be incorporated into the phospholipid-containing particles as integral or peripheral membrane proteins ($\beta_2$-glycoprotein-I, prothrombin, protein S, protein C, etc).

| APC:  | activated protein C |
| ATIII: | antithrombin III |
| D.S.: | dermatan sulfate |
| GAG: | glycosaminoglycans |
| HCII: | heparin cofactor II |
| HEP: | heparan sulfate or heparin |
| PC: | protein C |
| PS: | protein S |
| TF: | tissue factor |
| TFPI: | tissue factor pathway inhibitor |
| TM: | thrombomodulin |
| II: | prothrombin |
| IIa: | thrombin |

Other roman numerals stand for the corresponding blood coagulation factors, activated when followed by "a" and inactivated when followed by "i".

Figure 1:
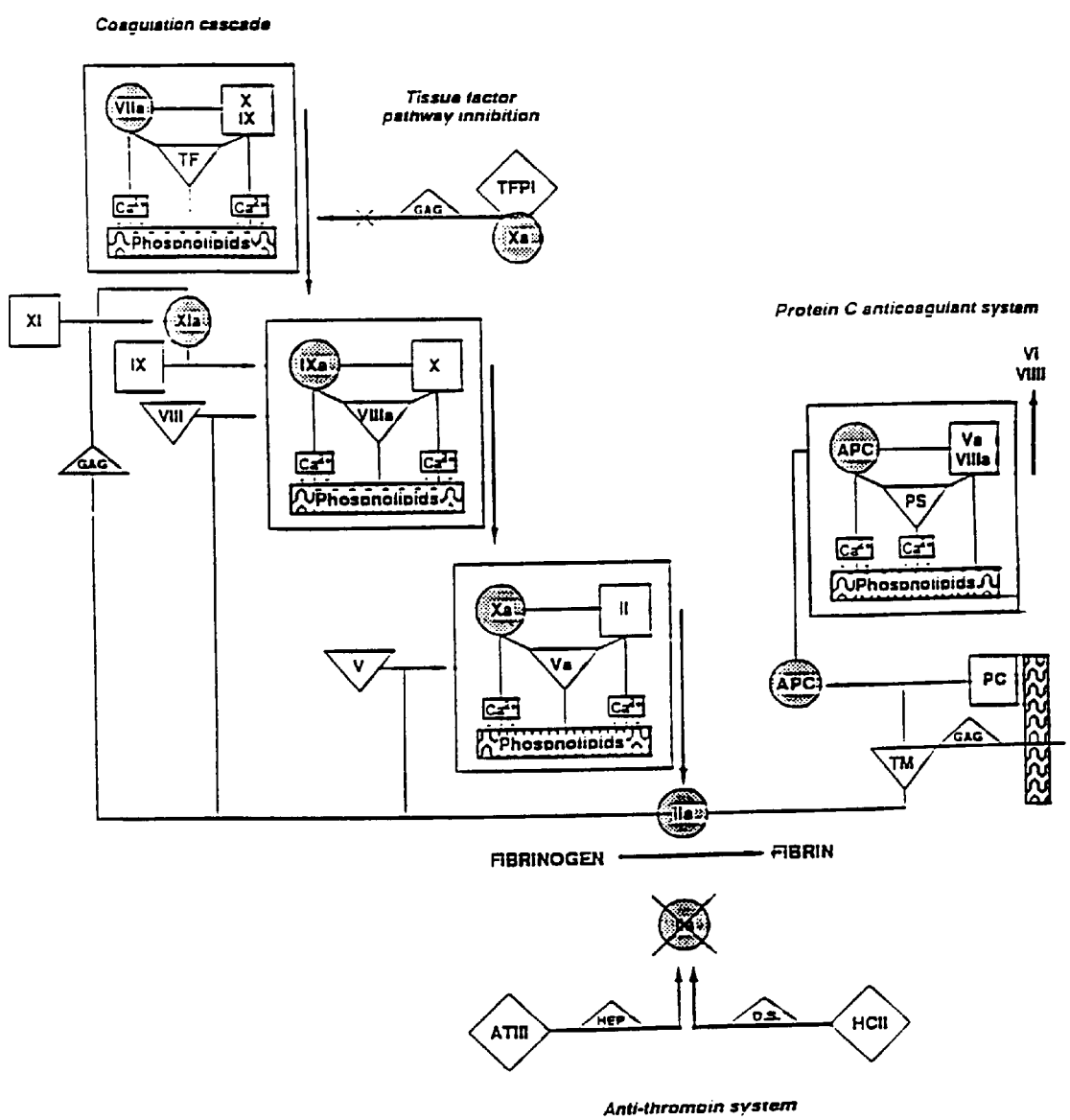
FIG. 1 shows the blood coagulation system.
Figure 2:
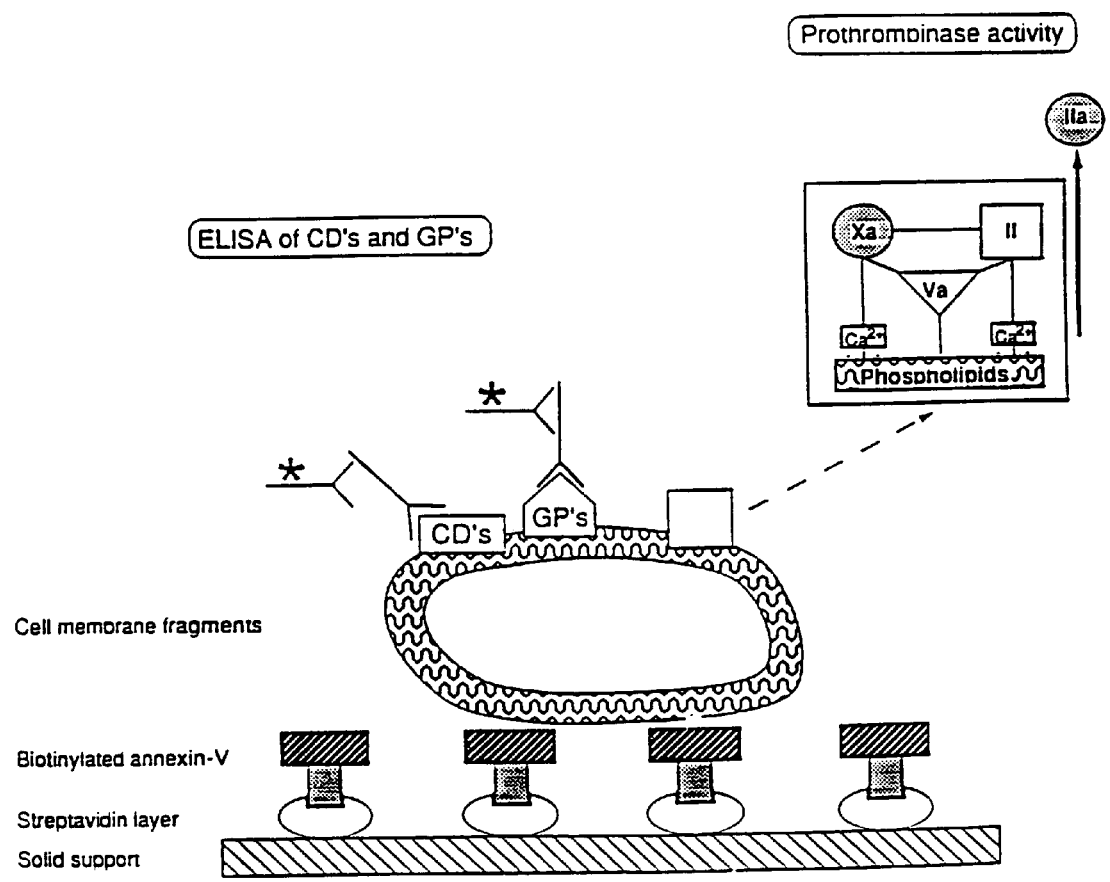

FIG. 2 shows the principle of the detection of circulating microparticles or stimulated procoagulant cells or cell fragments by an ELISA of CD's and/or GP's or by prothrombinase activity.

GP's: Glycoproteins

CD's: Cluster of differentiation antigens

Figure 3:
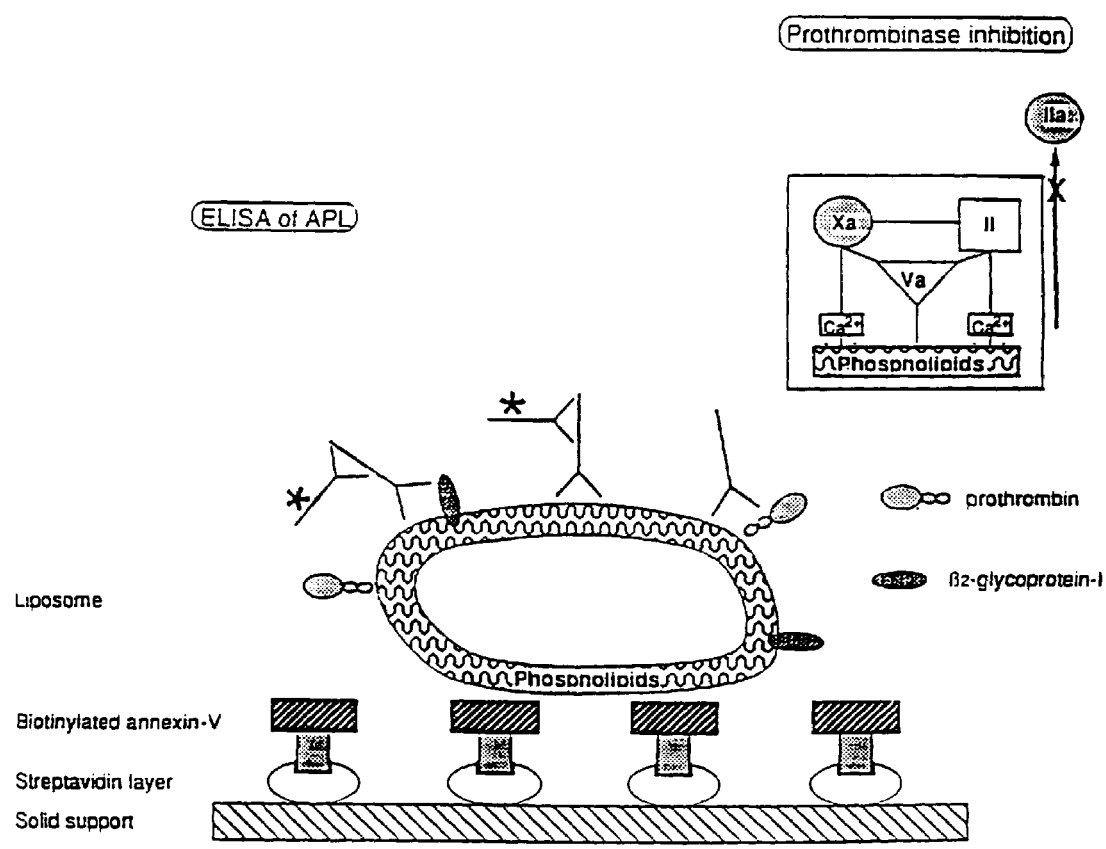

FIG. 3 shows the principle of the detection of phospholipid-binding antibodies by ELISA of APL (phospholipid-binding antibody).

Figure 4:
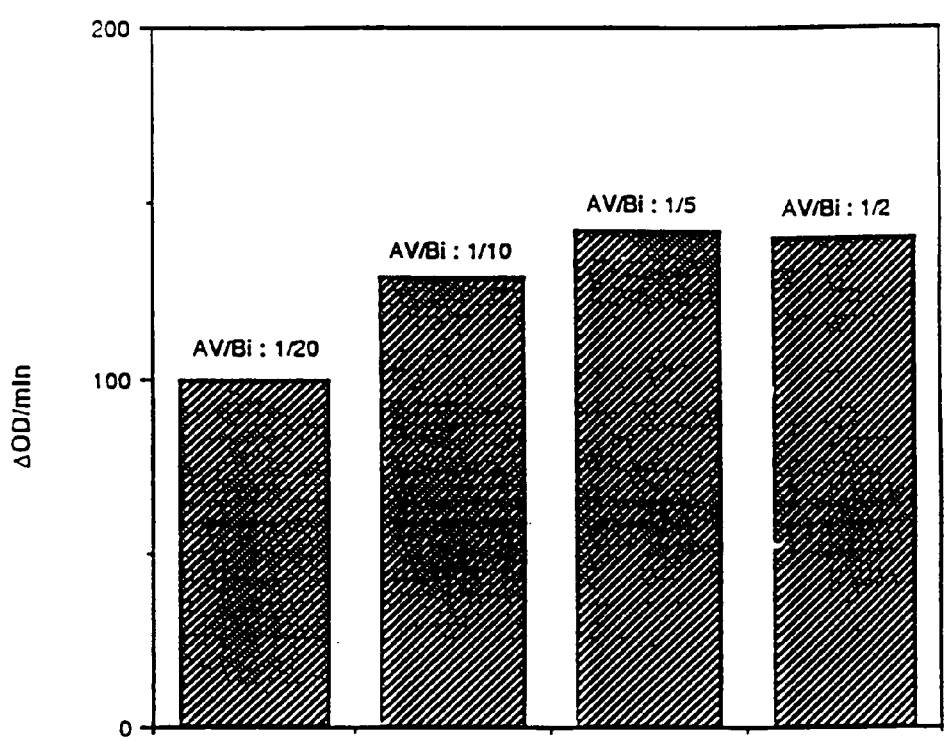
Figure 5:
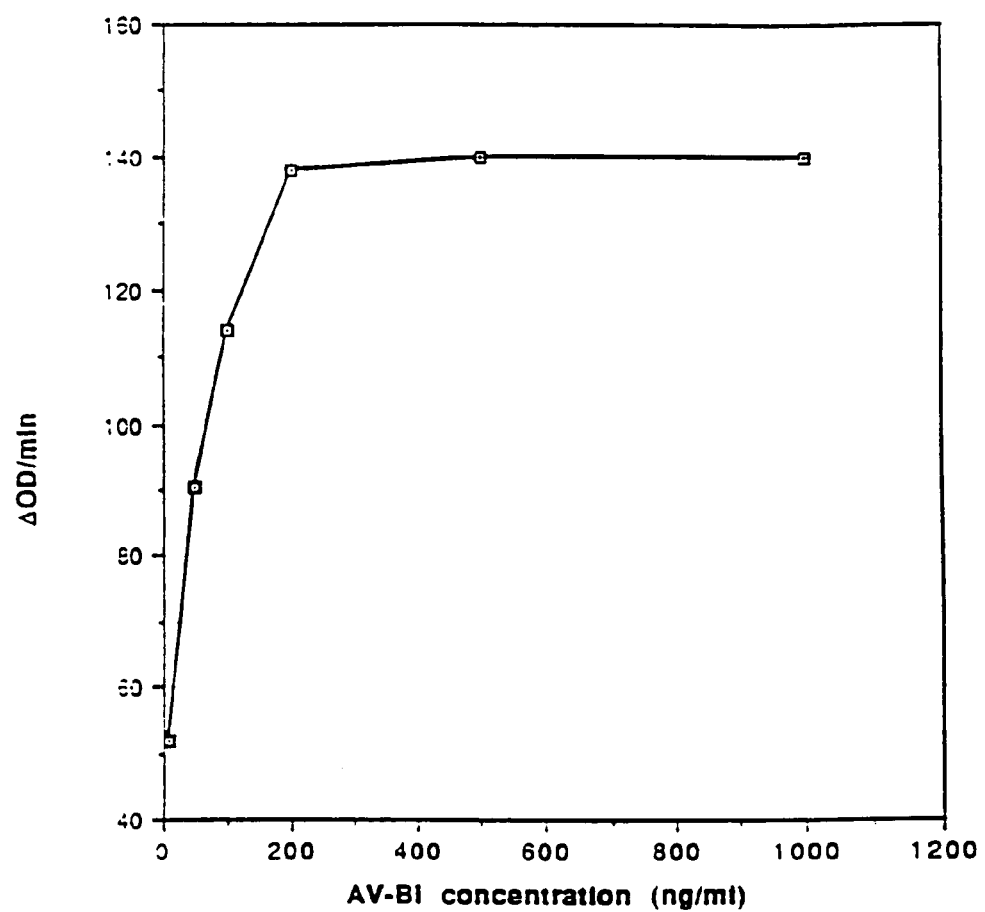
Figure 6:
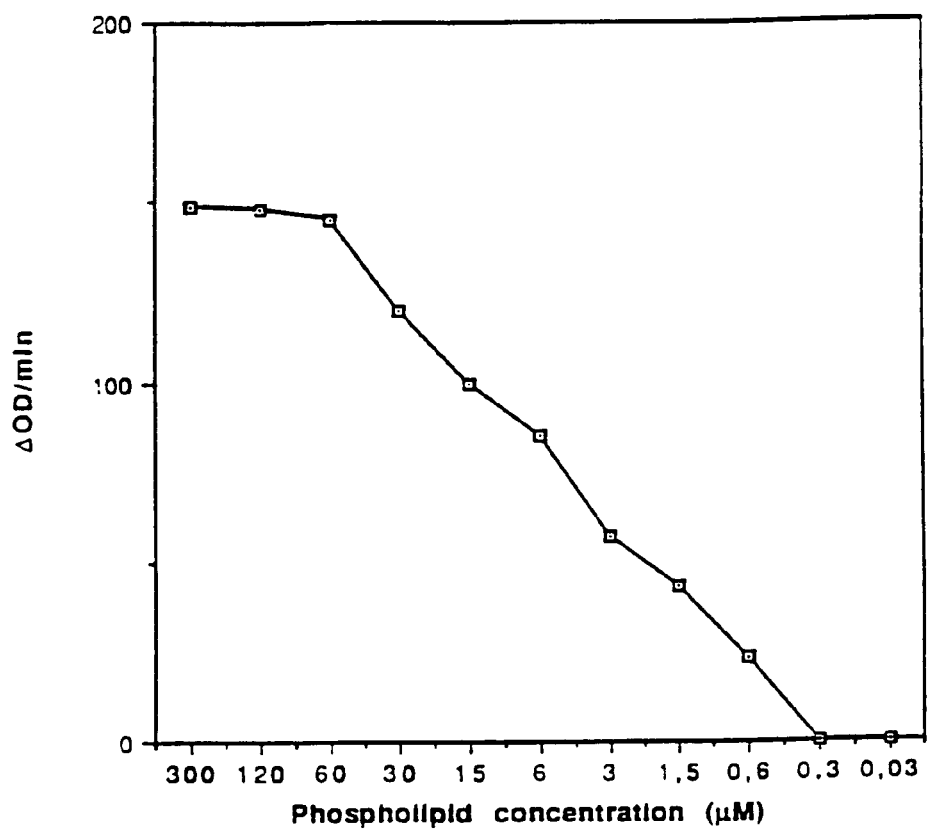

FIG. 4 shows the effect of the biotinylated ratio of annexin-V on the prothrombinase assay AV/Bi: biotinylated ration of annexin-V ΔOD/min: optical density per minute FIG. 5 shows the effect of the biotinylated annexin-V (AV-Bi) concentration on the prothrombinase assay ΔOD/min: optical density per minute FIG. 6 shows the effect of the phospholipid concentration on the prothrombinase assay.

ΔOD/min: optical density per minute

Figure 7:
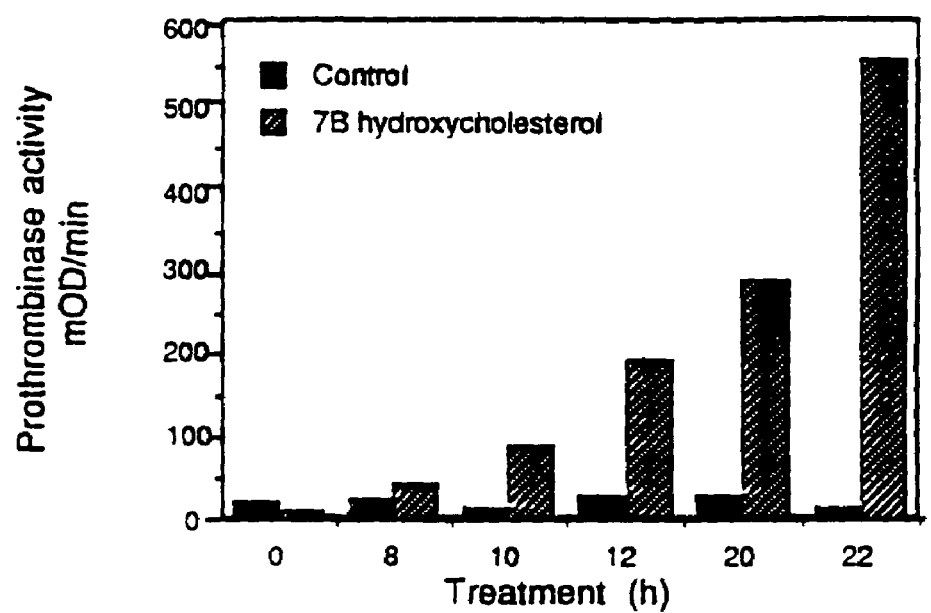

FIG. 7 shows the prothrombinase activity in the supernatant of U937 cells treated with oxysterols for the induction of apoptosis.

Figure 8:
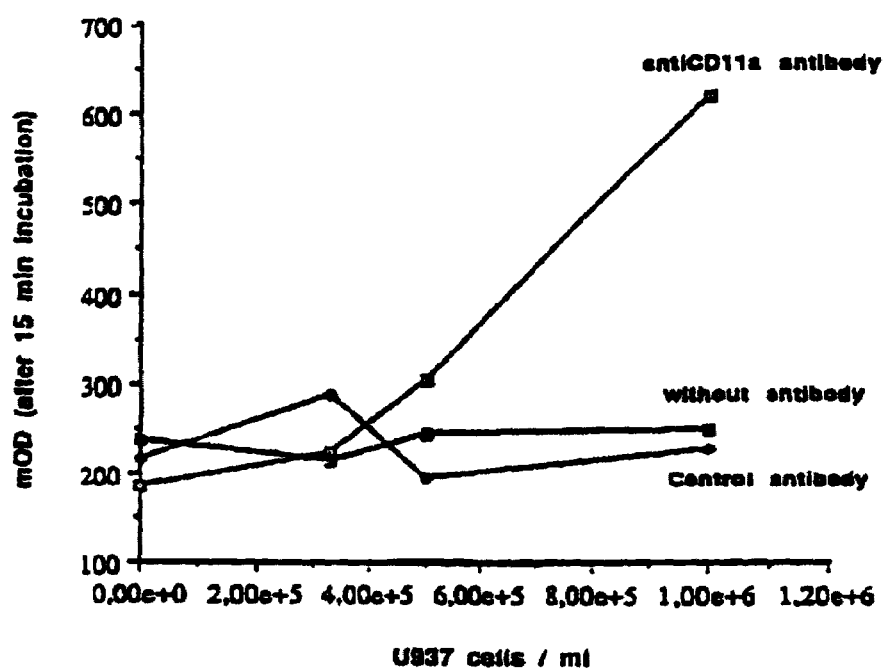

FIG. 8 shows the detection of specific membrane antigen CD11a present at the surface of microparticles captured by biotinylated annexin Va complexed to SA-coated microtiterplates.

Figure 9:
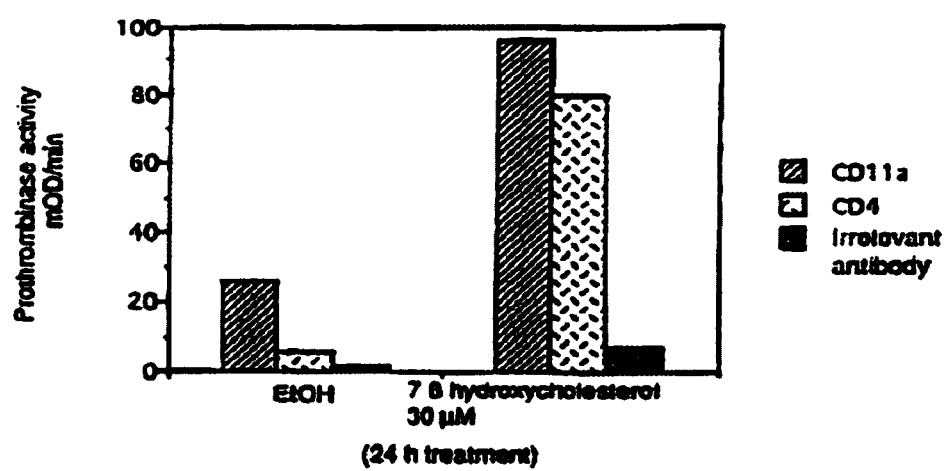

FIG. 9 shows capture of microparticles bearing specific antigens by corresponding insolubilized antibodies.

Figure 10:
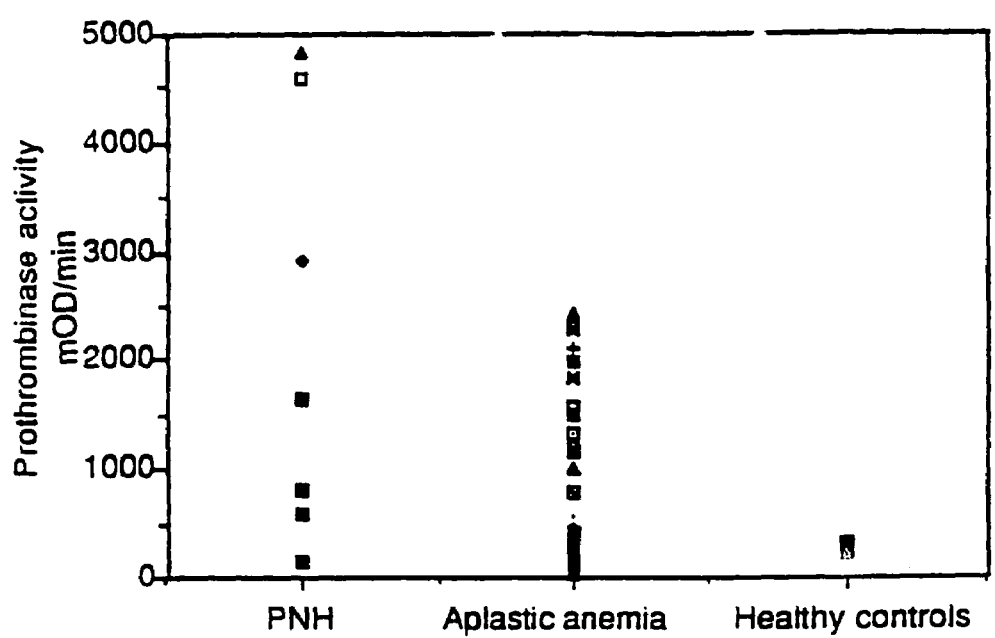

FIG. 10 shows procoagulant microparticle detection in plasma from patients with PNH.

Figure 11:
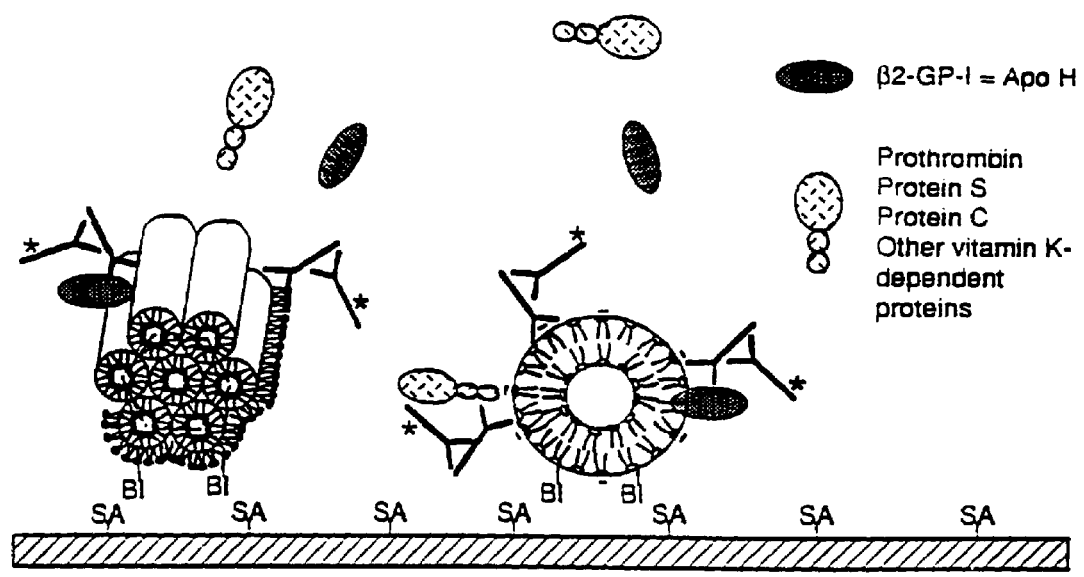

FIG. 11 shows immobilization of different phospholipd antigens onto streptavidin-coated microtitration plates for solid phase detection of phospholipid-binding antibodies.

Left: hexagonal phase phospholipids, right: bilayer phospholipids; SA and B1 stand for streptavidin and biotin respectively.

The invention will be described in greater detail in the following examples.

EXAMPLE 1

Proteins and Reagents

Human blood coagulation factor X and prothrombin were purified from vitamin K-dependent protein concentrates free of common viral contaminants (Freyssinet J.-M. et al., Interference of blood coagulation vitamin K-dependent proteins in the activation of human protein C. Biochem J. 256 (1988), 501–507). Human α-thrombin (3,000 National Institutes of Health (NIH) units/mg of protein) was prepared from purified prothrombin according to Freyssinet J.-M. et al., Interference of blood coagulation vitamin K-dependent proteins in the activation of human protein C. Biochem J. 256 (1988), 501–507. Factor Xa was obtained from purified factor X as described in Freyssinet J.-M. et al., Activation of human protein C by blood coagulation factor Xa in the presence of anionic phospholipids. Biochem J. 261 (1989), 341–348. Factor V was purchased from Diagnostica Stago (Asnières, France). Human placenta annexin V (placental anticoagulant protein-I) was purified according to Funakoshi et al. (Funakoshi T. et al., Human placental anticoagulant protein: isolation and characterization. Biochemistry 26 (1987) 5572–5578) and characterized as published in Ravanat C. et al., Use of annexin-V and its binding to lipid vesicles. J. Mol. Biol. 226 (1992), 1271–1278. 1-O-n-octyl-β-D-glucopyranoside, streptavidin-coated microtitration plates (BM # 1487051), biotin-X-OSu (BM # 1008978) and Chromzym TH were from Boehringer Mannheim (Mannheim, Germany). Phosphatidyl choline and phosphatidyl serine from bovine brain, human serum albumin and calcium ionophore A23187 were products from Sigma Chemical Co. (St. Louis, Mo.). Fluorescent membrane probe (red fluorescence) 1,1'-dihexadecyl-3,3,3',3'-tetramethyl indocarbocyanine ($DilC_{16}(3)$) was from Molecular Probes (Eugene, Oreg.). Chromogenic substrates N-α-benzylocarbonyl-D-arginyl-L-glycyl-L-arginine-p-nitroanilide-dihydrochloride (S-2765) and H-D-phenylalanyl-L-pipecolyl-L-arginine-p-nitroanilide dihydrochloride (S-2238) were purchased from Chromogenix AB (Mölndal, Sweden). D-Phenylalanyl-Prolyl-Arginyl chloromethyl ketone (PPACK) and 1,5-dansyl-Glutamyl-Glycyl-Arginyl chloromethyl ketone (Dns-GGACK), two potent irreversible inhibitors of thrombin and factor Xa respectively, were obtained from Calbiochem (San Diego, Calif.). All other reagents were of the highest available purity grade.

Liposomes

Reference liposomes made of 33% phosphatidyl serine and 67% phosphatidyl choline (mol/mol) were prepared by the dialysis method according to Freyssinet J.-M et al., Activation of human protein C by blood coagulation factor Xa in the presence of anionic phospholipids. Biochem J. 261 (1989), 341–348.

For the phospholipid vesicle preparation (phosphatidyl serine/phosphatidyl choline 33/66 (mol/mol) 3 mM) the following reagents were used:

L-α-Phosphatidyl-L-serine from bovine brain (Sigma): PS 18.18 mg/ml (chloroform solution)

L-α-Phosphatidyl choline, type III-B from bovine brain (Sigma): PC 10 mg/ml (chloroform solution)

Buffer A (without detergent):
Tris 50 mM, NaCl 150 mM, $NaN_3$ 0.02% (w/v), pH 7.5

Buffer B (with detergent):
n-octyl β-D-glucopyranoside 2% (w/v) buffer A

Procedure Use Chloroform Rinsed Glassware

55 μl of PS were mixed with 200 μl of PC, evaporated under nitrogen flow at room temperature, resuspended in 1 ml of buffer B and dialysed against buffer A.

In some experiments the $DilC_{16}(3)$ probe was added to the phospholipid mixture at a final molar ratio of 0.1% before dialysis which allowed its incorporation into the resulting bilayer structures. When analyzed in the frozen-hydrated state by cryo-electron microscopy, the liposomes appeared mostly unilamellar, rather spherical and had a mean diameter of 150 nm, with extremes at 30 and 300 nm (Pigault C. et al., Formation of two-dimensional arrays of annexin-V on phosphatidylserine-containing liposomes. J. Mol. Biol. 236 (1994) 199–208). Phospholipid molar concentrations were determined assuming an average molecular weight of 780 for each species. For use as capture standards by insolubilized annexin-V, liposomes were diluted in 50 mM Tris buffer, pH 7.5, containing 0.1 M NaCl and 1 mM $CaCl_2$. The characteristics of $DilC_{16}(3)$-labeled liposomes appeared comparable to that of microparticles shed from either cell type including platelets (see below) when analyzed by flow cytometry (Dachary-Prigent J. et al., Annexin-V as a probe of aminophospholipid exposure and platelet membrane vesiculation: A flow cytometry study showing a role for free sulfhydryl groups. Blood 81, 2554–2565).

Cells

Megakaryocyte cell lines HEL and MEG-01 are routinely cultivated following recommended procedures from the ATCC (American Type Culture Collection, Rockville, Md.). Human monocytes were harvested and maintained in culture as described in Sattan N. et al., Monocyte vericulation, J. Immunol. 153 (1994), 3245–3255: A mechanism for dissemination of membrane-associated procoagulant activities following stimulation by lipopolysaccaride (1994), submitted. Either type of cell was adjusted to $1.10^7$ cells/ml before treatment with 3 μM calcium ionophore for 3 min in the presence of 2 mM $CaCl_2$ at room temperature, in order to induce maximum microparticle shedding and phosphatidyl serine exposure. Cells and corresponding supernatants were separated by centrifugation at 12,000 g for 1 min at room temperature. Cell pellets were resuspended in a volume equal to the original one.

Samples from Patients or Control Subjects

Blood samples were collected by vein puncture in 0.14 M tri-sodium citrate at a final volume ratio of 9:1. Platelet rich plasma (PRP) was obtained by centrifugation at 180 g for 15 min at room temperature. Platelets were counted using a microscope. Platelet poor plasma (PPP) was obtained by centrifugation of PRP at 12,000 g for 1 min at room temperature. Another procedure to obtain PPP constited of staring from plasma harvested after centrifugation of whole citrated blood at 1,500 g for 10 min. at room temperature and centrifuged a second time at 12,000 g for 1 min. at room temperature. Just before recalcification, PPACK and Dns-GGACK were added to samples at a final concentration of 10 μM each. When used undiluted, samples were recalcified by addition of $CaCl_2$ at a final concentration of 30 mM just before being in contact with insolubilized biotinylated annexin-V. This starting calcium concentration was 2-fold less for each 2-fold dilution of samples. As the final citrate concentration is 14 mM, at least 21 mM of calcium is necessary to complex the excess of citrate. Hence, incremental calcium with respect to the 21 mM value should, in theory, be sufficient to allow the interaction between insolubilized annexin V (see below) and cell fragments bearing exposed phosphatidyl serine. However, in the mM range, calcium should allow the optimal binding of fragments bearing at least 10% phosphatidyl serine, in the 10 mM range this threshold can be lowered to 2% as published in ref. Pigault C. et al., Formation of two-dimensional arrays of annexin-V on phosphatidylserine-containing liposomes. J. Mol. Biol. 236 (1994) 199–208.

Biotinylation of Annexin-V and Preparation of Streptavidin-Biotin-Annexin-V-Coated Microtitration Plates Biotinylation of annexin-V was achieved at various biotin to protein molar rations ranging from 20/1 and 2/1.

| REAGENTS | |
|---|---|
| Biotinylation buffer: | 75 mM $KH_2PO_4$, 200 mM NaCl, pH 7.7 |
| Biotin solution: | 11.4 mM Biotin-X-OSu (MW = 454.5) in DMSO |
| Storage buffer: | 75 mM $KH_2PO_4$, 200 mM NaCl, Lysin 10 mM, pH 7.7 |

0.5 mg of annexin V is dialysed overnight at 4° C. against 200 ml of Biotinylation buffer. Annexin V (MW=35000) is then diluted to 1 mg/ml ($\epsilon_{AV}$=0.6).

Biotin solution is added to annexin V at the following ratio:

AV/biotin (mol/mol)=1/5

After 90 min at 25° C., the reaction is stopped by adding IM Lysine/HCl to a final concentration of 10 mM. The biotinylated annexin V is finally dialysed overnight at 4° C. against Storage buffer. This biotinylated annexin V can be stored for months at −80° C., without detectable loss of anti-phospholipid potential.

Biotinylated annexin-V (annexin-$V^{Bi}$) was insolubilize onto streptavidin-coated microtitration plates by contact of 100 μl/well of annexin-$V^{Bi}$ solution in 50 mM Tris buffer, pH 7.5, containing 0.1 M NaCl and 3 mg/ml albumin, at concentrations ranging from 50 ng/ml to 1 μg/ml, during 30 min at room temperature. The plates were then washed 3 times with 200 μl of the above buffer and immediately used for capture of activated cells or fragments.

Capture of Activated Cells or Derived (Micro)Particles

100 μl of PRP or 200 μl of PPP samples recalcified and supplemented with thrombin and factor Xa inhibitors as described above, or 100 μl of either cell suspension or corresponding supernatant, or 100 μl of liposomes was added per well. Incubation was allowed to proceed for 30 min at room temperature and was followed by 4 washing steps by 200 μl of 50 mM Tris buffer, pH 7.5, containing 0.1 M NaCl and 1 mM $CaCl_2$. In some control experiments liposomes were used instead of PRP or PPP samples, in other ones 3 mM EDTA was used instead of calcium. Plates supposed to bear activated cells or fragments were immediately used for detection of procoagulant phospholipids by prothrombinase assay.

Prothrombinase Assay

Blood clotting factor concentrations have been determined to ensure that phosphatidyl serine concentration is the rate-limiting parameter of linear reactions of activation of prothrombin to thrombin. In any case less than 20% of total protein substrate was converted into its activated form. Measurements were performed in triplicate in 96-well streptavidin-annexin-$V^{Bi}$-coated microtitration plates in 50 mM Tris buffer containing 120 mM NaCl, 2.7 mM KCl 1.5 mM $CaCl_2$ and 3 mg/ml albumin, adjusted to pH 7.5, in a final incubation volume of 150 μl.

Phosphatidyl serine presence was detected through its ability to promote the activation of prothrombin (2 μM) by factor Xa (10 pM) in the presence of factor V(a) (50 pM) and $CaCl_2$ (1.5 mM). The 5-fold excess of factor V with respect to factor Xa enables to minimize the possible contribution of factor V couterpart attached to or released by cells. Incubation was allowed to proceed for 2 h for platelet samples, cell suspensions and corresponding supernatants, or 15 min for control liposomes, at 37° C. in either case. Prothrombin activation was stopped by addition of an excess of EDTA, i.e. 3 mM final concentration. Chromogenic substrate for thrombin, S-2238 or Chromozym TH, was then added at final concentration of 0.1 mM. Linear absorbance changes recorded at 405 nm were converted to concentration of generated thrombin by reference to a standard curve constructed with known amounts of thrombin. In controls either factor Xa or prothrombin, or both were omitted.

Inhibition assays of prothrombinase activity by soluble annexin V were carried out by adding this phospholipid antagonist at a final concentration of 1.5 μM in the respective media just before coagulation factors. The aim of the latter verification was to ascertain the phospholipid-dependent character of the measured generation of thrombin.

EXAMPLE 2

Effect of Biotinylation Ratio of Annexin-V

Different protein to biotin molar ratios, ranging from 1/2 to 1/20, were tested in the prothrombinase assay of example 1. 1/5 to 1/10 ratio yielded the best labeling condition with almost no loss of phospholipid-binding capacity or ability to retain liposomes or activated cells or derived fragments when insolubilized (see FIG. 4). No attempt to quantify the number of biotin molecules linked per molecule of annexin-V was made since the procedure appeared rather reproducible without alteration of annexin-V properties (determined by insolubilization of annexin-$V^{Bi}$ onto streptavidin-coated microtitration plates and determination of phospholipid capture capacity by prothrombinase assay using liposomes).

Effect of Annexin-$V^{Bi}$ and Phospholipid Concentration

Several conditions were tested with respect to annexin-$V^{Bi}$ concentration as well as the initial protein to biotin ratio. As above the protein to biotin ratio was varied between 1/2 to 1/20 while the annexin-$V^{Bi}$ concentration range was 50 ng/ml to 1 μg/ml. Phospholipids were added under the form of liposomes at concentrations ranging from 0.03 to 300 μM.

The best combination was achieved when annexin-V was biotinylated at a protein to biotin ratio of 1/5 and used at 400 ng/ml for complexation to insolubilized streptavidin (FIG. 5). Under these conditions saturation occurred at 60 μM phospholipid (FIG. 6) which corresponds roughly to the maximum surface packing assuming that liposomes are spherical and have an average diameter of 1,500 Å. At saturation the amount of generated thrombin was ~1 nM/min.

EXAMPLE 3

Capture of Cultured Cells or Derived Fragments by Insolubilized Annexin-$V^{Bi}$ In order to further ascertain the ability of insolubilized annexin-$VB^{i}$ to retain cells or shed fragments bearing phosphatidyl serine exposed at their outer surface, lysed platelets, or ionophore-activated cells or corresponding supernatant were incubated in annexin-V-containing wells as described above.

The supernatant of platelets lysed at an initial concentration of $15 \times 10^7$ cells/ml was a source of procoagulant phospholipids which allowed to reach saturation under the same conditions as liposome suspension containing 60 µM phospholipid. It is interesting to emphasize that the phospholipid concentration contributed by $15 \times 10^6$ platelets/ml is about 130 µM, i.e. half the optimal liposome concentration. However, the proportion of phosphatidylserine in liposomes is at least three times higher than that of lysed platelets since it cannot be expected to be greater than 10% (mol/mol) in the latter case where phospholipid scrambling is considered as maximum (Zwaal R. F. A. et al., Platelets and coagulation. In: Zwaal R. F. A. et al., eds., Blood coagulation. Amsterdam: Elsevier Science Publishers B.V. (1986), 141–169). This indicates that inducible phospholipid-dependent procoagulant activity is more efficient than that of liposomes bearing spartaneously expressed phosphatidylserine.

The same saturation amplitude as that observed with liposomes was obtained with monocytes or supernatant but after two hour incubation in the prothrombinase assay instead of 10 min which corresponds to a thrombin generation rate of ~85 pM/min. The value measured with HEL or MEG-01 or respective supernatants were ~4 to 5 times smaller. The phospholipid composition and distribution in monocyte, HEL and MEG-01 plasma is not known but it can be reasonably anticipated that ionophore-activated monocytes would exhibit the same procoaguant activity as lysed platelets when adjusted to the same concentration while that of HEL and MEG-01 cells would remain consistently lower.

EXAMPLE 4

Capture of Circulating Activated Platelets or Shed Microparticles by Insolubilized Annexin-$V^{Bi}$ and Determination of Associated Prothrombinase Activity Nine samples from 16 patients and 8 control subjects were examined after preparation and used without dilution as described in example 1. The results of prothrombinase activity determinations are summarized in the following table 1, values being normalized to $3 \times 10^8$ platelets/ml.

TABLE 1

| Sample origin | Pathology | Platelet count in whole blood ($\times 10^{11}$/ml) | Platelet count in RPR ($\times 10^8$/ml) | PPP prothrombinase activity (pM of thrombin generated/min) | PPP prothrombinase activity (ΔDO/min) | PRP prothrombinase activity (pM of thrombin generated/min) |
|---|---|---|---|---|---|---|
| F . . . E. | Heart failure | 2.18 | 1.25 | 519 | 934 | ? |
| C . . . L. | Pneumonia | 1.79 | 1.50 | 285 | 514 | ? |
| H . . . A. | Myeloproliferative syndrome, diabetes | ? | 2.5 | 99.5 | 179 | 45 |
| B . . . F. | Lupus | 3.83 | 1.65 | 97 | 174 | ? |
| F . . . C. | Alcoholic intox., polynevritis, anti-MAG | ? | 1.4 | 96.1 | 173 | 272.5 |
| K . . . O. | Cancer, Metastasis (lung?), Heart transplantation | 2.05 | 1.4 | 94 | 169 | ? |
| M . . . H. | Lupus | 1.6 | 1 | 77 | 138 | ? |
| H . . . M. | Transplantation (Cyclosporin, Immunosuppression, Corticoids), | 1.98 | 1.75 | 58 | 104 | ? |
| S . . . K. | Alcoholic intox | 1.46 | 2 | 53 | 96 | ? |
| W . . . J. | Non-inflammatory heart failure | 2.21 | 2.5 | 42 | 76 | ? |
| F . . . M. | SLE, APL syndrome, fetal loss | ? | 2 | 39.2 | 70.5 | 68.3 |
| H . . . M.-A. | Cancer (ovary) | 1.85 | 1.35 | 33 | 59 | ? |
| V . . . N. | Not determined, at hospital admission | ? | 4.5 | 32.8 | 59 | 389.4 |
| M . . . M.-M. | Lupus | 2.17 | 2.5 | 12 | 22 | ? |
| S . . . R. | Polyarthritis, AHT, Glomenilonephritis Heart an renal failure | 1.79 | 0.9 | 9 | 17 | ? |
| G.L. | Hydrocephalitis Inflammatory syndrome | 3.29 | 3.5 | 9 | 16 | ? |
| S . . . N. | control | ? | 3 | 21 | 38 | ? |
| R . . . J.-P. | control | ? | 3.15 | 15 | 27 | 28.3 |
| D . . . C. | control | ? | 2.95 | 15 | 27 | ? |
| E . . . V. | control | ? | 3.5 | 13 | 23.5 | ? |
| B . . . U. | control | ? | 6.3 | 5.3 | 9.5 | 17.2 |
| K . . . E. | control | ? | 5.5 | 4.7 | 8.5 | 13.3 |
| D . . . I. | control | ? | 4.9 | 3 | 5.5 | 21.1 |
| T . . . F. | control | ? | 6.4 | 2.2 | 4 | 4.4 |

SLE: systemic lupus erythemalosus,
APL: anti-phospholipid
MAG: myelin-associated glycosaminoglycans
AHT: arterial hyper tention
ΔDO/min/1800 = 1 nM of thrombin generated/min
? = not detected

EXAMPLE 5

Determination of Phosphatidylserine-Containing Apoptotic Bodies Derived from U937 Cells U937 cells are grown in a humidified 5% $CO_2$ atmosphere at 37° C., using RPMI 1640 medium with Glutamax-I, supplemented with 10% heat-inactivated fetal calf serum, 1 mM sodium pyruvate, non-essential amino acids and gentamicin icin at 5 µg/mL Cells are usually plated at an initial conentration of $1.10^5$/ml. Apoptosis induction is achieved by 40 µM 7β hydroxycholesterol- or 5 µg/ml actinomycin D-treatment of U937 cells at 37° C. during 8 to 24 hours. Cells have to be seeded at 3 to $4.10^5$ cells per ml 6 h before treatment. Cell supernatant is obtained by centrifugation of treated cells at 500 g during 7 min and $CaCl_2$ is added to a final concentration of 10 mM before addition of 200 µl/well of supernatant. For each experiment, a control without 7β hydroxycholesterol or actinomycin D has to be performed and culture medium containing 10% fetal calf serum should also be tested. It has to be emphasized that the content of microparticles of 10% fetal calf serum was low, probably due to removal of most of the cell fragments at sterilizing ultrafiltration. The amount of captured microparticles is determined using the prothrombinase assay.

Biotinylated annexin V (AV-Bi) (see example 1) was diluted to 400 ng/ml in TBS, 1 mM $CaCl_2$, 3 g/l HSA. 100 µl/well were added to streptavidin-coated microtitration plates (Boehringer Mannheim GmbH) and incubated at room temperature for 30 min. Excess of AV-Bi was eliminated by washing steps with TBS, 1 mM $CaCl_2$. 200 µl/well cell supernatant as described above and $CaCl_2$ 10 mM were added and incubated for 30 min. After three washing steps with TBS, 1 mM $CaCl_2$ the prothrombinase assay was performed.

Prothrombinase Assay: (Dilutions in TBS, 1 mM $CaCl_2$, 3 g/l HSA)

| | |
|---|---|
| TBS, 1 mM $CaCl_2$, 3 g/l HSA: | 90 µl/well |
| Factor V 0.5 nM (50 nM, diluted 1/100): | 10 µl/well |
| Factor II 0,65 mg/ml (FlI 1 mg/ml, diluted to 0.65 mg/ml): | 20 µl/well |
| Factor Xa 83 pM (2.9 µM diluted 1/35000): | 20 µl/well |
| $CaCl_2$ 20 mM (1 M, diluted 1/50): | 10 µl/well |
| 2 h incubation at 37° C. | |
| EDTA Mg 20 mM (80 mM, diluted 1/4): | 50 µl/well |
| Chromozym-TH 1.52 mM (3.8 mM, diluted 1/2.5): | 50 µl/well |

The liar absorbance changes at 405 nm were recorded by using a microplate reader equipped with a kinetics software. The results of the prothrombinase assay are shown in FIG. 7.

The Prothrombinase Activity is Correlated with DNA Analysis by Flow Cytometry (Table 2)

TABLE 2

| | 7β-hydroxycholesterol treatment (hours) | | | | | |
|---|---|---|---|---|---|---|
| | 0 h | 8 h | 10 h | 12 h | 20 h | 22 h |
| % of hypodiploid DNA | 2.75 | 9.43 | 12.58 | 18.31 | 35.03 | 41.54 |

The results show the exposure of phosphatidylserine associated with apoptosis, and provide evidence that the degree of cell death can be easily estimated by prothrombinase assay after capture of resulting vesicles.

In another experiment the origin of the apoptotic cells was detected. For this, cryolysed U937 cells were used to generate lysis fragments as described above. These apoptotic cell fragments, bear CD11a as a target antigen. The cells were captured by AV-bi on a SA-plate as described above and detected by POD-labeled antibodies to CD11a which are commercially available. The results are shown in FIG. 8. It was possible to detect these cells by this antibody and thereby the origine of the cells could by detected.

Capture of Microparticles Derived from Apoptotic U937 Cells Using Specific Biotin-Labelled Antibodies Biotinylated antibodiy (anti CD4 or anti CD11a, Leinco Technology, diluted to 1 µg/ml in TBS, 1 mM $CaCl_2$, 3 µl HSA) are added to streptavidin-coated microtitration plates (100 µl/well) an d incubated 30 min at room temperature. Excess of biotinylated antibody was eliminated by washing steps with TBS (3×250 µl). Cell supernatant of U937 cells after induction of apoptosis as described above was added (200 µl/well) and incubated 2 h at room temperature. The plates were washed with TBS (3×250 µl).

Prothrombinase assay: (dilutions in TBS, 1 mM $CaCl_2$, 3 g/l HSA)

| | |
|---|---|
| TBS, 1mM $CaCl_2$, 3 g/l HSA: | 90 µl/well |
| Factor V 0.5 nM (50 nM, diluted 1/100): | 10 µl/well |
| Factor II 0,65 mg/ml (FlI 1 mg/ml, diluted to 0.65 mg/ml): | 20 µl/well |
| Factor Xa 83 pM (2.9 µM diluted 1/35000): | 20 µl/well |
| $CaCl_2$ 20 mM (1 M, diluted 1/50): | 10 µl/well |

2 h incubation at 37° C.

| | |
|---|---|
| EDTA-$Mg^{2+}$ 20 mM (80 mM, diluted 1/4): | 50 µl/well |
| Chromozym-TH 1.52 mM (3.8 mM, diluted 1/2.5): | 50 µl/well |

The linear absorbance changes were recorded at 405 nm using a microplate reader equipped with a kinetics software.

The apoptotic cell derived microparticles are captured by the biotin-labelled antiCD4 or antiCD11a immobilized onto streptavidin-coated microtitration plate. The amount of captured microparticles can be determined using the prothrombinase say. The results are shown in FIG. 9.

These results are in agreement with a higher amount of CD11a antigen than CD4 in U937 cells.

EXAMPLE 6

Procoagulant Microparticle Detection in the Plasma of Patients with Paroxysmal Nocturnal Hemoglobinuria Paroxysmal nocturnal hemoglobinuria (PNH) is an acquired stem-cell disorder in which the glyoclipid-anchored membrane proteins, including the cell-surface complement inhibitors, CD55 and CD59, are partially or completely deleted from the plasma membrane of mature blood cells (45). This leads to hyperhemolysis resulting from hypersensitivity of red blood cells to activated complement. From a clinical point oif view, PNH is characterised by hemolytic anemia and hypercoagulable state that frequently leads to thrombosis. The hypercoagulability has been attributed to the hemolysis itself or to platelet defects or hyperactivation.

The plasma samples from several patients were investigated in order to show the ability of the system to assess the thrombotic risk potentially linked to this disease.

The activated cells and/or microparticles were captured with AV-Bi on a SA-coated microtiter plate as described above. The results are shown in FIG. 10.

All the prothrombinase activities arising from patient samples were higher than those from the healthy controls, except for one patient. This can be explained by the fact that this particular patient was recently transfused and did not present, at the time of analysis, deficient red blood cells or platelets with respect to CD55, CD58 and CD59. Other patients have a significant proportion of red blood cells and platelets in which CD55, CD58, and CD59 are not detectable. The association of PNH and aplastic anemia raises the as yet unresolved issue whether these two disorders are different presentation of the same disease. In any case, an important proportion of the patients with aplastic anemia secondarily develop a PNH clone.

Controls

All the above observations were controlled with respect to the specificity of the capture of activated cells or derived fragment by annexin-$V^{Bi}$. When retained by annexin-$V^{Bi}$, liposomes or either of activated cells or shed fragments could be released by an excess of EDTA, i.e. no prothrombinase activity could be detected after such a treatment. An amazing observation is that of the possible recycling of the system: once a measurement has been performed, a simple washing with Tris buffer containing EDTA instead of calcium is sufficient to restore its capture capacity.

No prothrombinase activity could be measured when either of factor Xa or prothrombin were omitted in the prothrombinase assay and only traces of it were observed in the absence of factor V. Annexin-$V^{Bi}$ is stable for weeks when stored below 0° C.

EXAMPLE 7

Detection of Phospholipid-Binding Antibodies (APL) and Annexin II-Binding Antibodies (AAII)

Phosphatidylserine is thought to be a determinant of reticuloendothelial recognition leading to elimination of circulating membrane debris (Allen T., Willimason. & Schlegel R. A. Phosphatidylserine as a determinant of reticuloendothelial recognition of liposome models of the erythrocyte surface. Proc. Natl. Acad. Sci. USA, 1988, 85, 8067–8071). However, it is conceivable that in case of continuous cell membrane damage the reticuloendothelial system could be overwhelmed and that excess of anionic phospholipid could progressively trigger coagulation reactions. Under such circumstances the release of sequestered phospholipids could be at the origin of the anti-phospholipid syndrome associated with thrombosis (McNeil H. P., Chesterman C. N. & Krilis S. A. Immunology and clinical importance of antiphospholipid antibodies, Adv. Immunol., 1991, 49, 193–280). The presence of APL is associated with an increased risk of thrombosis, thrombocytopenia and fetal loss, making their detection of prime importance.

Phospholipid Vesicle Preparation for use in the Detection of Phospholipid-Binding Antibodies
Card/PC/Chol/PE-B1 2.7/10.5/4/1 (mol) 1 mM Cardiolipin (Card) from bovine heart, 5 mg/mL ethanol solution
MW: 1500 g/mol
L-α-Phosphatidylcholine (PC) from bovine brain, 10 mg/ml, chloroform solution
MW: 778 g/mol
Cholesterol (Chol) from porcine liver, 40 mg/ml, chloroform solution
MW: 386 g/mol
N-(6-(biotinoyl)amino)hexanoyl)dipalmitoyl-L-α-phosphatidylethanolamine
(PE-B1), 5 mg/ml chloroform solution
MW: 1132 g/mol Buffer A (without detergent):
(Tris Hcl 9.52 g, Tris base 1.77 g, NaCl 13.2 g, NaN$_3$ 10% 3 ml, complete to 1.5l with H$_2$O)
Tris 50 mM
NaCl 150 mM
NaN$_3$ 0.02% (w/v)
pH 7.5

Buffer B (with detergent):
n-octyl β-D-glucopyranoside 2% (w/v): 0.1 g in 5 ml of buffer A
(BM, Ref: 737062)

Procedure 33.3 µl of Card were mixed with 33.3 µl of PC, 1.6 µl of Chol and 9.2 µl of PE-B1 on ice, evaporated under nitrogen flow at room temperature, resuspended in 500 µl of buffer B, dialysed against 3×500 ml of buffer A at 4° C. during 18 to 24 h and stored at 4° C. (no more than one month).

Detection of Phospholipid-Binding Antibodies

Card/PE-B1 vesicles 1 mM were diluted to 1/150 in TBS, 1 mM CaCl$_2$, 3 g/l HSA, 100 µl/well were added to streptavidin-coated microtitration plates, incubated for 30 min at 4° C., washed with TBS, 1 mM CaCl$_2$ (4×200 µl/well), neutralized by 30 min incubation at 4° C. with 10% bovine serum (v/v) n TBS, 1 mM CaCl$_2$ (100 µl/well).

The wells were washed with TBS, 1 mM CaCl$_2$ (3×200 µl/well), serum sample diluted to 1/100 (or more in case of strong positive) in TBS, 1 mM CaCl$_2$, bovine serum 10% (v/v) was added (50 µl/well), incubated for 2 h at 4° C. and washed with TBS, 1 mM CaCl$_2$ (3×200 µl/well), GAHu/IgG(H+L)HRPO diluted to 1/1000 in TBS, 1 mM CaCl$_2$, bovine serum 10% (v/v) (50 µl/well) was added, incubated for 1 h at 4° C. and washed with TBS, 1 mM CaCl$_2$ (3×200 µl/well). OPD at 0.4 mg/ml was added (50 µl/well), incubated for 4.5 min at room temperature and H$_2$SO$_4$ 6 N added (50 µl/well). The absorbance was read at 492 mm.

Phospholipid Vesicle Preparation for Use in the Detection of Annexin-II-Binding Antibodies
PS/PC/PE-Bi 25/74/1 (mol) 3 mM
L-α-Phosphatidyl-L-serine (PS) from bovine brain, 10 mg/ml chloroform solution
MW: 780 g/mol
L-α-Phosphatidylcholine (PC) from bovine brain, 10 mg/ml, chloroform solution
MW: 778 g/mol
N-(6-(biotinoyl)amino)hexanoyl)dipalmitoyl-L-α-phosphatidylethanolamine
(PE-B1) 5 mg/mL chloroform solution
MW: 1132 g/mol Buffer A (without detergent):
(Tris HCl 9.52 g, Tris base 1.77 g, NaCl 13.2 g, NaN$_3$ 10% 3 ml, complete to 1.5l with H$_2$O)

Tris mM
NaCl 150 mM
NaN$_3$ 0,02% (w/v)
pH 7.5

Buffer B (with detergent):
n-octyl β-D-glucopyranoside 2% (w/v): 0.1 g in 5 ml of buffer A
(BM, Ref: 737062)

Procedure

100 μl of PS were mixed with 300 μl of PC and 12 μl of PE-Bi on melting ice, evaporated under nitrogen flow at room temperature, resuspended in 1700 μl of buffer B and dialysed against 3×500 ml of buffer A at 4° C. during 18 to 24 h.

Detection of Annexin-II-Binding Antibodies

PS/PC/PE-Bi vesicles 25/74/1 (mol) 3 mM were diluted to 1/400 in TBS, 1 mM CaCl$_2$, 3 g/l HSA 100 μl/well were added to streptavidin-coated microtitration plates, incubated for 30 min at 4° C. and washed with TBS, 1 mM CaCl$_2$ (3×200 μl/well). Annexin II diluted to 10 μg/ml in TBS, 1 mM CaCl$_2$, 10% bovine serum (v/v) was added (100 μl/well), incubated for 30 min at 4° C. and washed with TBS, 1 mM CaCl$_2$ (3×200 μl/well). Serum sample diluted to 1/100 (or more in case of strong positive) in TBS, 1 mM CaCl$_2$ 50 μl/well), bovine serum 10% (v/v)as added, incubated for 2 h at 4° C. and washed with TBS, 1 mM CaCl$_2$ (3×200 μl/well). GAHu/IgG(H+L)/HRPO Goat Anti-Human/IgG (H+L)/ Horseradish Peroxidase, 0.7 mg/ml diluted to 1/1000 in TBS, 1 mM CaCl$_2$, (50 μl/well), bovine serum 10% (v/v) was added incubated for 1 h at 4° C. and washed with TBS, 1 mM CaCl$_2$ (3×200 μl/well). OPD: o-Phenylenediamine dihydrochloride (Sigma, Ref: P 9187) at 0.4 mg/ml (50 μl/well) was added and incubated 5 min at room temperature. H2SO4, 6 N (50 μl/well) was added and the absorbance read at 492 nm.

Comparison of the APL and AAII Assays According to the Invention with Methods of the Art Most of the solid phase immunoassay detecting APL use cardiolipin coated onto polystyrene as antigen. These lipids coated on plates adopt a monolayer film organization. In the assays according to the invention hexagonal phase or bilayer phospholipids of various composition are used. These are tightly and reproducibly bound to the solid support via for example biotin/streptavidin interaction (see FIG. 11). This certainly presents an advantage for the investigation of the nature and diversity of APL and possible clinical associations. The major reason for using bilayer or hexagonal phase phospholipids in solid assays is that these models of organization are much closer to membrane and shed fragment structures.

10 samples found to be positive in methods according to the state of the art (flow cytometrie and Cardiolisa-assay from Biomedical Diagnostics, France) were tested on the APL and AAII assays. The results are presented in table 3.

All positive 10 samples were positive in the APL assay. The patient samples LA and BE were positive in the AAII detection assay. In the AAII assay antibodies against a complex of amexin II and phospholipids will be detected.

TABLE 3

| Serum | APL Flow cytometry | | | APL ELISA* | | | Our APL detection essay | Our AAII detection essay |
| --- | --- | --- | --- | --- | --- | --- | --- | --- |
| | TBS-alb | TBS-alb+ apo H | TBS-serum | TBS-alb | TBS-alb+ apo H | TBS-serum | | |
| pool 1 | neg | neg | neg | neg | neg | neg | 0,200 | 0,250 |
| pool 2 | neg | neg | neg | neg | neg | neg | 0,154 | 0,208 |
| CY | neg | ± | neg | neg | neg | x1,5 | 0,235 | 0,231 |
| OK | neg | neg | neg | neg | neg | x.2 | 0,298 | 0,328 |
| PR | neg | + | neg | neg | x3 | x3 | 0,351 | 0,291 |
| KA | ++ | ++ | ++ | x15 | x30 | x15 | 0,364 | 0,337 |
| CI | + | + | + | neg | x3 | x5 | 0,367 | 0,231 |
| BA | ± | ± | ± | neg | neg | x1,5 | 0,577 | 0,296 |
| FU | + | ++ | + | neg | x10 | x10 | 0,602 | 0,325 |
| LA | ++ | ++ | ++ | x3,5 | x7 | x5 | 0,707 | 0,806 |
| BE | ++ | ++ | ++ | x2 | x8 | x6 | 0,786 | 0,465 |
| CH | + | ++ | + | x2 | x2 | x2 | 1.081 | 0.226 |

*Each ELISA result is expressed as a multiple of the OD of the control pool. ELISA tests are performed using monolayer phospholipids as the capture antigen. Our APL detection assay uses bilayer phospholipids, and β$_2$-glycoprotein-1 brought about by 10% bovine serum used for sample dilutions.

The invention claimed is:

1. A method for determining a thrombotic or prethrombotic state, disease or risk therefor in an individual being screened for said state disease or risk, comprising:
    obtaining a body fluid sample from the individual, said sample suspected of comprising a member selected from the group consisting of circulating microparticles, stimulated procoagulant cells and mixtures thereof;
    incubating the sample with a solid phase-bound purified receptor specific for a phospholipid, under conditions to form an immobilized complex on the solid phase of the purified receptor and any said member present in said sample;
    washing the incubated solid phase to remove unbound components; and
    determining a level of prothrombinase activity of the washed immobilized complex, wherein an elevated level of prothrombinase activity determined for the immobilized complex compared with a level determined for normal body fluid samples indicates a thrombotic or prethrombotic state, disease, or elevated risk therefor in the individual.

2. The method according to claim 1, wherein the prothrombinase activity of the complex is determined by reacting the bound said member of the complex with a reagent comprising factor V, factor Xa, prothrombin (factor II) and calcium-ions for a time sufficient for activation of prothrombin to thrombin (factor IIa), stopping the reaction by complexation of the calcium-ions, and determining amount of thrombin generated in said reaction by reacting the generated thrombin with its ability to hydrolyze a chromogenic substrate therefor and comparing with a standard curve.

3. The method according to claim 1, wherein inhibitors of thrombin, Factor Xa or both thrombin and Factor Xa are present during the incubating step.

4. The method according to claim 1, wherein prothrombinase activity of said complex is determined directly on said solid phase.

5. The method according to claim 1, wherein prothrombinase activity of said complex is determined by determining prothrombinase activity of the bound said member after removing said bound member from said complex.

6. The method according to claim 1, wherein said purified receptor is annexin V.

7. The method according to claim 6, further comprising adding calcium ions in the incubating and determining steps.

8. The method of claim 1, wherein said purified receptor is bound directly to the solid phase.

9. The method according to claim 1, wherein said purified receptor is bound indirectly to the solid phase.

10. The method according to claim 1, wherein said purified receptor is bound to the solid phase via a specific binding pair comprising a first and a second binding pair member, and wherein said first binding pair member is attached to the solid phase and said second binding pair member is coupled to said purified receptor.

* * * * *